(12) United States Patent
Puhl et al.

(10) Patent No.: US 11,685,759 B2
(45) Date of Patent: Jun. 27, 2023

(54) METHOD FOR OBTAINING CRYSTALLINE 2'-FUCOSYLLACTOSE

(71) Applicant: BASF SE, Ludwigshafen am Rhein (DE)

(72) Inventors: Michael Puhl, Ludwigshafen am Rhein (DE); Sebastian Wloch, Ludwigshafen am Rhein (DE); Peter Oedman, Saint Joseph, MO (US); Anne-Catrin Letzel, Ludwigshafen am Rhein (DE); Hartwig Schroeder, Ludwigshafen am Rhein (DE); Jacek Malisz, Ludwigshafen am Rhein (DE); Daniel Seibert-Ludwig, Ludwigshafen am Rhein (DE); Emiel Jan Kappert, Ludwigshafen am Rhein (DE); Chung Huan Wong, Ludwigshafen am Rhein (DE); Michael Barros Gross, Ludwigshafen am Rhein (DE); Martin Viertelhaus, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/286,474

(22) PCT Filed: Oct. 17, 2019

(86) PCT No.: PCT/EP2019/078147
§ 371 (c)(1),
(2) Date: Apr. 18, 2021

(87) PCT Pub. No.: WO2020/079114
PCT Pub. Date: Apr. 23, 2020

(65) Prior Publication Data
US 2021/0388014 A1  Dec. 16, 2021

(30) Foreign Application Priority Data

Oct. 18, 2018  (EP) .................................... 18201228
Nov. 15, 2018  (EP) .................................... 18206491
Aug. 23, 2019  (EP) .................................... 17193228

(51) Int. Cl.
C07H 1/08 (2006.01)
C07H 3/06 (2006.01)

(52) U.S. Cl.
CPC .............. *C07H 1/08* (2013.01); *C07H 3/06* (2013.01); *C07B 2200/13* (2013.01)

(58) Field of Classification Search
CPC ..................................... C07H 3/06; C07H 1/08
See application file for complete search history.

(56) References Cited

U.S. PATENT DOCUMENTS 5,438,124 A   8/1995   Matta et al.

FOREIGN PATENT DOCUMENTS

| CN | 102676604 A | 9/2012 |
|---|---|---|
| DE | 4442074 A1 | 5/1996 |
| DE | 19745750 A1 | 5/1999 |
| EP | 2058468 A2 | 5/2009 |
| EP | 2857410 A1 | 4/2015 |
| WO | 2010/070104 A1 | 6/2010 |
| WO | 2010/070616 A2 | 6/2010 |
| WO | 2010/115934 A1 | 10/2010 |
| WO | 2010/115935 A1 | 10/2010 |
| WO | 2011/150939 A1 | 12/2011 |
| WO | 2012/007481 A2 | 1/2012 |
| WO | 2012/097950 A1 | 7/2012 |
| WO | 2012/112777 A2 | 8/2012 |
| WO | 2013/139344 A1 | 9/2013 |
| WO | 2014/009921 A2 | 1/2014 |
| WO | 2014/086373 A1 | 6/2014 |
| WO | 2015/188834 A1 | 12/2015 |
| WO | 2016/038192 A1 | 3/2016 |
| WO | 2016/095924 A1 | 6/2016 |
| WO | 2017/153452 A1 | 9/2017 |
| WO | 2018/164937 A1 | 9/2018 |

OTHER PUBLICATIONS

International Preliminary Report on Patentability received for PCT Patent Application No. PCT/EP2019/078147, dated Apr. 29, 2021, 8 pages.
International Search Report and Written Opinion received for PCT Patent Application No. PCT/EP2019/078147, dated Nov. 26, 2019, 10 pages.

*Primary Examiner* — Jonathan S Lau
(74) *Attorney, Agent, or Firm* — Faegre Drinker Biddle & Reath LLP

(57) ABSTRACT

The present invention relates to a method for obtaining crystalline 2'-fucosyllactose from a 2'-FL raw material, which contains 2'-FL as a main constituent and at least 0.5% by weight, frequently at least 1% by weight, in particular at least 2% by weight, more particularly at least 5% by weight, and especially at least 8% by weight,based on the total amount of mono-and oligosaccharides in the raw material, of one or more mono- or oligosaccharides different from 2'-FL, where the method comprises a)providing a solution of the 2'-FL raw material in water, which does not contain more than 10% by weight, preferably not more than 7% by weight, more preferably not more than 5% by weight of organic solvents, based on the total amount of water; b) effecting the crystallization of 2'-FL from the solution provided in step a) by inducing conditions of a controlled super saturation in the solution; and c) separating crystalline 2'-FL from the mother liquor, and where during controlled supersaturation in step b) not more than 10% by weight, preferably not more than 7% by weight, more preferably not more than 5% by weight of organic solvents are present, based on the total amount of water present during step b).

17 Claims, 6 Drawing Sheets

METHOD FOR OBTAINING CRYSTALLINE 2'-FUCOSYLLACTOSE

CROSS-REFERENCE TO RELATED APPLICATIONS

This application is a national stage application (under 35 U.S.C. § 371) of PCT/EP2019/078147, filed Oct. 17, 2019, which claims benefit of European Application Nos. 18201228.6, filed Oct. 18, 2018, 18206491.5, filed Nov. 15, 2018, and 19193228.4, filed Aug. 23, 2019, all of which are incorporated herein by reference in their entirety.

The present invention relates to a method for obtaining crystalline 2'-fucosyllactose from a 2'-fucosyllactose raw material and in particular to a method for selectively obtaining either the hydrate form A or the anhydrate form II of 2'-fucosyllactose.

BACKGROUND OF THE INVENTION

2'-Fucosyllactose (CAS No.: 41263-94-9: α-L-fucopyranosyl-(1→2)-O-β-D-galactopyranosyl-(1→4)-D-glucopyranose, hereinafter 2'-FL) is an oligosaccharide, which is found in relatively large quantities in breast milk. It has been variously reported that the 2'-FL present in breast milk causally reduces the risk of infection in newborns who are breast fed (see e.g. Weichert et al., Nutrition Research, 33 (2013), Volume 10, 831-838; Jantscher-Krenn et al., Minerva Pediatr. 2012, 64 (1) 83-99; Morrow et al., J. Pediatr. 145 (2004) 297-303). 2'-FL is therefore of particular interest as a constituent of food supplements, particularly as additive for humanized milk products, especially for infant nutrition.

The preparation of 2'-O-fucosyllactose by classical chemical or biochemical means has been variously described in the literature (for classic chemical means see e.g. U.S. Pat. No. 5,438,124, WO 2010/070616, WO 2010/115934, WO 2010/115935, WO 2016/038192 and WO 2017/153452; for biochemical means see e.g. Drouillard et al. Angew. Chem. Int. Ed. 45, 1778 (2006), WO 2010/070104, WO 2012/007481, WO 2012/097950, WO 2012/112777, WO 2013/139344, WO 2014/086373, WO 2015/188834 and WO 2016/095924).

Principally, the production of is 2'-FL by fermentation process using transformed microorganisms such as transformed E.coli is promising both for economic and environmental reasons. However, isolation of 2'-FL is tedious and usually requires
- separating the supernatant containing the product by centrifugation,
- adsorption of the product on a bed of activated charcoal that was washed with water to eliminate water-soluble contaminants like salts, amino acids and protein fragments,
- elution of the product with alcohol or aqueous alcohol, and
- last not least, separation of 2'-FL from other carbohydrates like lactose and fucose by gel permeation chromatography or flesh chromatography on charcoal celite beds. The main drawback of this isolation method has been the need for chromatographic separation in order either to get the pure substance or to obtain at least a mixture that is enriched in the target compound but still contains undesired derivatives. Although repeated chromatographic separations can result in the improvement of the purity, its high cost and relatively long technological time to handle the feed solution and the column packing, to carry out the separation and optionally to regenerate the packing, especially in large or industrial scale, can be disadvantageous and/or cumbersome.

Crystallization or recrystallization is principally a simple and cheap method for isolating a product from a reaction mixture and separating it from contaminations thereby obtaining a purified substance. Isolation or purification that uses crystallization may therefore render the whole technological process robust and cost-effective, thus it is principally advantageous and attractive compared to other procedures. While crystallization of 2'-FL, which has been prepared by classical organic synthesis, is an efficient means for isolation or purification of 2'-FL, crystallization cannot be easily applied to 2'-FL, which has been prepared by non-classical organic synthesis, because the product obtained by fermentative production of 2'-FL contains a significant amount of by products, including in particular oligosaccharides other than 2'-FL, but also monosaccharides. As these mono- and oligosaccharides have comparable polarities and, hence, comparable solubilities, they are difficult to separate by crystallization processes.

Kuhn et al. (Chem. Ber. 1956, page 2513) report that 2'-FL which has been purified by repeated chromatography does not readily crystallize but remains a syrup. The authors mention that few crystals of 2'-Fl formed when leaving an aqueous solution of 2'-FL standing for a prolonged period. Larger amounts of crystalline 2'-FL could be obtained only from solutions containing mixtures of water with a considerable amount of organic solvents.

WO 2014/086373 describes a method for obtaining an oligosaccharide such as 2'-FL from a fermentation broth, which comprises freeze-drying of the fermentation broth, preferably after having removed proteins therefrom, to produce a dry powder, treating the dry powder with an aliphatic alcohol, such as methanol, to dissolve the oligosaccharide which is then crystallized from the alcoholic solution. The method is tedious as it requires previous freeze drying of the fermentation broth and the use of organic solvents.

WO 2015/188834 describes a method for crystallization of 2'-FL from an aqueous solution containing 2'-FL and a fucosylated oligosaccharide, such as difucosyllactose, which method comprises fermentative production of 2'-FL by using genetically modified cells having a recombinant gene that encodes a 1,2-fucosyltransferase, separating the supernatant from non-carbohydrate solids and contaminants and adding $C_1$-$C_4$-alkanols in order to effect crystallization of 2'-FL.

WO 2016/095924 describes a method for crystallization of 2'-FL from an aqueous solution containing 2'-FL and a fucosylated oligosaccharide, such as difucosyllactose, which method comprises providing an aqueous solution of 2'-FL and the fucosylated oligosaccharide as described in WO 2015/188834 and addition of acetic acid to the aqueous solution in order to effect crystallization of 2'-FL.

WO 2014/009921 describes different polymorph forms of 2'-FL. While polymorph form B can be obtained by recrystallization of pure 2'-FL, e.g. pure polymorph form A, from water, purification of a 2'-FL containing raw material, which additionally contains considerable amounts of mono- or oligosaccharides different from 2'-FL is not described therein.

WO 2018/164937 describes a process for crystallizing 2'-FL from an aqueous solution, which requires precipitating 2'-FL from an aqueous supersaturated solution at a temperature of greater than 60° C. By this method, the crystalline anhydrate of 2-FL, i.e. form II of 2'-FL, is obtained, which is described in WO 2011/150939.

The methods for obtaining crystalline still require considerable amounts of organic solvents during crystallization, which are difficult to remove, as they are frequently entrapped in the crystalline material. Especially for baby and the use of organic solvents is not acceptable, as it always bears the risk that the organic solvent cannot be completely removed.

SUMMARY OF THE INVENTION

There is still a need for an efficient process for obtaining crystalline 2'-FL from a 2'-FL raw material, which contains considerable amounts of mono- and oligosaccharides other than 2'-FL, such as lactose, acetylated 2'-FL, fucosylated lactose other than 2'-FL, and fucosylated lactulose, from aqueous solution of such raw materials, in in particular form aqueous solutions obtained by a fermentation process. The method should in particular allow the avoidance of organic solvents and provide 2'-FL in high purity and high yield. It has been found that 2'-FL can be efficiently and reliably crystallized from an aqueous solution of a 2'-FL raw material, which contains considerable amounts of mono- and oligosaccharides other than 2'-FL, by inducing conditions of controlled supersaturation in the aqueous solution and thereby effecting selective crystallization of 2'-FL. Inducing conditions of controlled supersaturation in the aqueous solution of 2'-FL raw material allows for efficient crystallization without the use of considerable amounts of organic solvents during crystallization. This is quite surprising, because 2'-FL is highly soluble in water and even pure 2'-FL hardly crystallizes from water and the considerable amounts of mono- and oligosaccharides contained in the 2'-FL raw material should further hamper crystallization of 2'-FL.

Therefore, the present invention relates to a method for obtaining crystalline 2'-fucosyllactose from a 2'-FL raw material, which contains 2'-FL as a main constituent and at least 0.5% by weight, frequently at least 1% by weight, in particular at least 2% by weight, more particularly at least 5% by weight, and especially at least 8% by weight, based on the total amount of mono- and oligosaccharides in the raw material, of one or more mono- or oligosaccharides different from 2'-FL, where the method comprises
a) providing a solution of the 2'-FL raw material in water, which does not contain more than 10% by weight, preferably not more than 7% by weight, more preferably not more than 5% by weight of organic solvents, based on the total amount of water;
b) effecting the crystallization of 2'-FL from the solution provided in step a) by inducing conditions of a controlled supersaturation in the solution at a temperature of preferably at most 60° C.; and
c) separating crystalline 2'-FL from the mother liquor, and where during controlled supersaturation in step b) not more than 10% by weight, preferably not more than 7% by weight, more preferably not more than 5% by weight of organic solvents are present, based on the total amount of water present during step b).

The method of the present invention is associated with several benefits. It allows efficient separation of 2'-FL from the other oligosaccharides, thereby obtaining 2'-FL in high yield and high purity of frequently more than 93%, in particular more than 95%, especially at least 97% or at least 98%, based on organic matter in the crystalline 2'-FL. In particular, the method does not require the use of organic solvents during crystallization and, therefore, the risk that the crystalline 2'-FL contains significant amounts of entrapped organic solvent is minimized. The process results in a mother liquor, which is colorless or almost colorless and thus can be subjected to further crystallization steps or re-introduced into the solution to be crystallized prior to effecting the crystallization.

By the method of the invention pure crystalline 2'-FL is obtained in the form of compact crystals.

Surprisingly, the method allows for selective crystallization of three polymorphic forms of 2'-FL in a reliable manner, namely
the anhydrate form II, which is described in WO 2011/150939 and which can be identified, e.g. by its characteristic reflections in an X-ray powder diffractogram, in particular the following reflections, quoted as $2\theta$ values: 16.98±0.2°, 13.65±0.2° and 18.32±0.2°, (at 25° C. and Cu-K$\alpha$ radiation);
the hydrate form A, which is described in WO 2014/009921 and which can be identified, e.g. by its characteristic reflections in an X-ray powder diffractogram, in particular the following reflections, quoted as $2\theta$ values: 18.86±0.2°, 17.05±0.2° and 9.89±0.2°, (at 25° C. and Cu-K$\alpha$ radiation); or
the hydrate form B, which is described in WO 2014/009921 and which can be identified, e.g. by its characteristic reflections in an X-ray powder diffractogram, in particular the following reflections, quoted as $2\theta$ values: 20.48±0.2°, 11.90±0.2° and 9.96±0.2°, (at 25° C. and Cu-K$\alpha$ radiation).

This is of particular importance for the registration of 2'-FL, which may require the reliable production of a specific polymorph form. The method allows for the selective preparation of either the crystalline anhydrate form II or the crystalline hydrate forms A or B of 2'-FL depending on the temperature at which the crystallization of 2'-FL is effected. In particular, the hydrate forms A or B will be obtained, if the crystallization of 2'-FL is effected at a temperature of at most 52° C., in particular at most 50° C., more particularly at most 48° C. and especially at most 45° C., e.g. in the range from 0 to 52° C., in particular from 0 to 50° C., more particularly from 0 to 48° C. and especially from 0 to 45° C., while the anhydrate form II will be obtained, if the crystallization of 2'-FL is effected at a temperature of above 52° C. in particular at a temperature of above 53° C. It is noted that the crystalline hydrate form B is initially formed, when effecting crystallization at a temperature of at most 52° C., in particular at most 50° C., more particularly at most 48° C. and especially at most 45° C. The crystalline hydrate form B, however, will convert into the crystalline hydrate form A upon drying.

Therefore the present invention also relates to a method for selectively obtaining either the crystalline hydrate forms A or B of 2'-FL or the crystalline anhydrate form II of 2'-FL from a 2'-FL raw material as defined herein, which method comprises performing the method for obtaining crystalline 2'-FL as described herein, provided that
either the crystallization of 2'-fucosyllactose is effected at a temperature in the range from 0° C. to 52° C., in particular from 0 to 50° C., more particularly from 0 to 48° C. and especially from 0 to 45° C. to obtain the crystalline forms A or B of 2'-fucosyllactose
or the crystallization of 2'-fucosyllactose is effected at a temperature of above 52° C., in particular of at least or above 53° C. and preferably at most 60° C. to obtain the crystalline form II of 2'-fucosyllactose.

DETAILED DESCRIPTION OF THE INVENTION

Here and in the following the terms 2'-FL and 2'-fucosyllactose are used synonymously and refer to $\alpha$-L-fucopyranosyl-(1→2)-O-β-D-galactopyranosyl-(1→4)-D-glucopyranose, including the α- and β-anomers and mixtures thereof.

The term "2'-FL raw material" as used herein refers to an oligosaccharide composition, which contains 2'-FL as a main constituent, in particular in an amount of at least 70% by weight, and a considerable amount, i.e. at least 0.5% by weight, frequently at least 1% by weight, in particular at least 2% by weight, more particularly at least 5% by weight, and especially at least 8% by weight, based on the total amount of mono- and oligosaccharides in the raw material, of one or more mono- or oligosaccharides different from 2'-fucosyllactose. In particular, the 2'-FL raw material from which crystalline 2'-FL is obtained by the method of the invention contains:

- 70 to 98% by weight, in particular 75 to 95% by weight, especially 78 to 92% by weight, based on the total amount of mono- and oligosaccharides in the raw material, of 2'-FL, and
- 2 to 30% by weight, in particular 5 to 25% by weight, especially 8 to 22% by weight, based on the total amount of mono- and oligosaccharides in the raw material, of one or more mono- or oligosaccharides different from 2'-fucosyllactose.

Typical mono- and oligosaccharides contained in the 2'-FL raw material, which are different from 2'-fucosyllactose, include but are not limited to lactose, fucosylated lactose other than 2'-FL, fucose, galactose, glucose, lactulose and fucosylated lactulose. These mono- and oligosaccharides are hereinafter termed "carbohydrate impurities or byproducts". The term "fucosylated lactose other than 2'-FL" as used herein includes any monofucosylated lactose other than 2'-FL. The term "fucosylated lactose other than 2'-FL" also includes any polyfucosylated lactose, in particular a difucosylated lactose which is also termed "difucosyllactose", such as 2,2'-O-difucosyllactose or 2',3-O-difucosyllactose.

Likewise, the term "fucosylated lactulose" used herein includes any monofucosylated lactulose and polyfucosylated lactulose, i.e. lactulose, which is fucosylated on the galactose moiety of lactulose by 1 or more, e.g. 1 or 2 fucose moieties.

The aforementioned carbohydrate impurities or byproducts may be formed during fermentation or under post-fermentation conditions. For example, fucosylated lactose other than 2'-FL may be formed as a result of a deficient, defective or impaired fucosylation other than an α-1,2-fucosylation on the galactose moiety of lactose, or of a fucose migration of 2'-FL under the fermentation or post-fermentation conditions or of fucose hydrolysis from multifucosylated lactose. Other carbohydrate impurities or byproducts may be formed by rearrangement such as lactulose and fucosylated lactulose or by hydrolysis such as fucose, glucose, galactose and lactose or may be unconsumed starting material, such as glucose or lactose.

In particular, the 2'-FL raw material contains at least one fucosylated lactose other than 2'-FL, in particular difucosyllactose. In particular, the amount of fucosylated lactose is in the range from 0.3 to 10% by weight, in particular 0.5 to 10% by weight, especially 1 to 10% by weight, based on the weight of mono- and oligosaccharides contained in the 2'-FL raw material. In particular, the 2'-FL raw material also contains at least one of lactulose and fucosylated lactulose or a mixture of both. In particular, the total amount of lactulose and fucosylated lactulose is in the range from 0.2 to 10% by weight, in particular 0.5 to 10% by weight, especially 1 to 10% by weight, based on the weight of mono- and oligosaccharides contained in the 2'-FL raw material.

In a first step a) of the method of the invention, an aqueous solution of 2'-FL raw material is provided which is then subjected to a crystallization in the second step b) under conditions of controlled supersaturation. Principally, any aqueous solution of 2'-FL raw material, which does not contain more than 10% by weight, preferably not more than 7% by weight, more preferably not more than 5% by weight of organic solvents, based on the amount of water contained therein, can be utilized in the method of the invention. It is essential for the invention that the aqueous solution of the 2'-FL raw material provided in step a) and which is subjected to the crystallization in step b) and also the water present during step b) does not contain considerable amounts of organic solvents. According to the present invention, the concentration of organic solvents in the solution provided in step a) does not exceed 5% by weight, in particular not exceed 2% and especially not exceed 1% by weight, based on the water contained in the solution provided in step a). Furthermore, the concentration of organic solvents in the water which is present during step b) does not exceed 10% by weight, preferably not exceed 7% by weight, more preferably not exceed 5% by weight, in particular not exceed 2% and especially not exceed 1% by weight, based on the water present during step b). In this context, the term "organic solvent" includes any organic compound, which has a boiling point at normal pressure in the range from 30 to 250° C. and includes, e.g. organic alcohols, in particular $C_1$-$C_4$-alkanols and $C_1$-$C_4$-alkanoic acids and any other organic compounds commonly used in the field of organic chemistry, in particular in the field of carbohydrate chemistry.

The aqueous solution may be an aqueous solution obtained from a biochemical process or from a conventional, i.e. chemical process.

The aqueous solution of the 2'FL raw material utilized in the method of the invention is preferably obtained from a biochemical process, such as a process, where 2'-FL is obtained by an enzymatic biocatalytic fucosylation of lactose or by a fermentation, as described e.g. in Drouillard et al. Angew. Chem. Int. Ed. 45, 1778 (2006), WO 2010/070104, WO 2012/007481, WO 2012/097950, WO 2012/112777, WO 2013/139344, WO 2014/086373, WO 2015/188834 and WO 2016/095924.

The fermentation broth usually contains in the supernatant of the culture medium at least 25 g/L of 2'-FL and may contain up to 120 g/L of 2'-FL or even more than 120 g/L of 2'-FL. In addition, the supernatant may also contain DFL, typically in amounts of about 1.5 to 20% by weight, relative to 2'-FL. The 2'-FL/DFL-mixture optionally contains fucosylated lactulose, which is produced in the culture medium, and/or lactose as unconsumed acceptor or further mono- or oligosaccharides.

If the aqueous solution of the raw material utilized in the method of the invention is obtained from a biochemical process, in particular from a fermentation, the obtained aqueous solution is frequently subjected to a post treatment prior to crystallization.

Such a post treatment may comprise a conventional demineralization step during which minerals, salts and other charged molecules are extracted from the aqueous solution before crystallization. The demineralization can be conducted by using conventional ion exchange resins, namely passing the aqueous solution through a cation exchange resin in $H^+$-form and an anion exchange resin in free base form. The cation exchange resin is preferably a strong exchanger, and the anion exchange resin is preferably a weak exchanger. The ion exchange resins, besides removing salts and charged molecules from the solution, can physically adsorb proteins, DNA and colorizing/caramel bodies that optionally left in the solution after previous purification steps. Alternatively, the demineralization can be conducted by means of a conventional electrodialysis. Additionally, adsorbents such as activated carbon may be optionally employed to remove colorizing compounds from the aqueous solution.

In some cases, it may be desirable to selectively remove some components of the aqueous solution of 2'-FL before crystallization. This may be achieved using different types of chromatography such as elution chromatography with or without a recycle loop or with continuous chromatographic processes such as simulated moving bed chromatography (SMB) including the variations thereof with asynchronous switching of the inlets and the outlets and/or variations of flow rates and/or feed concentration during a switch interval. Methods for using SMB for purification of aqueous solutions of oligosaccharides, such as 2'-FL, obtained from a fermentation have been described e.g. by T. Eiwegger et al., Pediatric Research, Vol. 56 (2004), pp. 536-540, CN 102676604 and EP 2857410, which can be applied by analogy for removing some components of the aqueous solution of 2'-FL before crystallization. A review of suitable methods for performing SMB can be found in M. Ottens et al., "Advances in process chromatography and application", Chapter 4.4.3, pp. 132-135, Woodhead Publishing Limited 2010 and the literature cited therein.

The solution obtained by any above ways can then be concentrated by either a conventional evaporation step or a conventional nanofiltration step, including ultrafiltration and diafiltration. Also, a microfiltration may be incorporated to remove proteins and macromolecules. A further final ("sterile") filtration before crystallization may be included to remove microbial contaminants.

It has been found beneficial, if the aqueous solution of 2'-FL raw material, which is provided in step a), is essentially free of water-insoluble solid material, i.e. the amount of water-insoluble material is less than 5000 ppm, in particular less than 1000 ppm, based on the 2'-FL contained therein, or at most 3000 ppm, in particular at most 1000 ppm, based on the weight of the aqueous solution of the 2'-FL raw material. Therefore, post treatment will preferably comprise a conventional clarification step. By this clarification step, cells fragments (debris) and proteins after fermentation are removed. Clarification is preferably prior to the charcoal treatment described below. The clarification can be done in a conventional manner, e.g. by sedimentation in centrifuge producing a clarified or partially clarified supernatant solution. Alternatively, the fermentation broth can be subjected to filtration step, e.g. to a micro-filtration or ultrafiltration, prior to subjecting it to the crystallization of step b). For example, ultrafiltration is performed in a conventional manner and removes high molecular weight components. The semipermeable membrane used for ultrafiltrating a 2'-FL fermentation broth can suitably have a cut-off of 5-50 kDa, preferably 10-25 kDa, more preferably around 15 kDa. Depending on the characteristics of the fermentation broth to be clarified, a combination of higher and lower cut off-membranes (in this order) within the above given range may be employed. Optionally, centrifugation or ultrafiltration can be followed by nanofiltration, during which the aqueous solution containing 2'-FL and carbohydrate by-products is concentrated in a conventional manner before it is treated with charcoal. In this nanofiltration step, its membrane can have a pore size that ensures retention of 2'-FL having a molecular weight of 488; so, typically, a 200-300 Da cut off membrane can be used.

In addition, post-treatment can further comprise a conventional charcoal treatment, which is preferably conducted before the demineralization step, in order to remove color bodies and optionally water-soluble bio-junk optionally left from previous purification steps. The carbohydrate compounds have strong affinity to be adsorbed on charcoal in aqueous medium; thus, water-soluble contaminants can be easily washed away with (distilled, preferably food-grade) water. The carbohydrates can then be eluted from the charcoal bed with alcohol or aqueous alcohol.

In step b) the crystallization of 2'-FL is effected by inducing conditions of a controlled supersaturation in the solution the 2'-FL raw material.

The concentration of 2'-FL in the aqueous solution, which is subjected to crystallization in step b), may generally vary from 400 to 750 g/L or from 500 to 750 g/L, in particular in the range from 500 to 700 g/L depending on the temperature of the aqueous solution. Frequently, the total concentration of carbohydrates, i.e. 2'-FL and mono- and oligosaccharides different from 2'-FL is in the range from 510 to 950 g/L, in particular in the range from 510 to 850 g/L.

Frequently, a dilute solution having a concentration of 2'-FL of at most 500 g/L, in particular at most 450 g/L, especially at most 400 g/L, e.g. in the range from 25 to 450 g/L or in the range from 50 to 400 g/L is provided in step a), which is then subjected to a concentration step, e.g. by evaporation of water, to a concentration of 2'-FL, where crystallization may occur, which is in particular in the range from 400 to 750 g/L or from 500 to 750 g/L, in particular from 420 to 720 g/L or from 510 to 720 g/L.

The concentration of the dilute solution to the desired concentration range for crystallization and the crystallization may be conducted in a single step, i.e. in the crystallization apparatus. It is also possible to perform a pre-concentration step first, where water is removed by evaporation, until a concentration 2'-FL is achieved, which is still below the solubility of 2'-FL under the equilibrium conditions. Then, this solution is introduced into the crystallization apparatus and in the thus concentrated solution conditions of controlled supersaturation are induced. The concentration of 2'-FL which corresponds to the solubility under conditions of equilibrium is also termed the equilibrium concentration or equilibrium solubility $c^*$ under the given conditions. As mentioned above, the concentration of 2'-FL in the solution, where conditions of controlled supersaturation are induced are typically in the range from 400 to 750 g/L, in particular in the range from 410 to 700 g/L or in the range from 410 to 650 g/L.

For the purpose of the invention, it has been found beneficial, if the concentration of 2'-FL in the aqueous solution of the 2'-FL raw material, which is subjected to crystallization in step b), does not exceed 650 g/L, in particular 630 g/L and is e.g. in the range from 400 to 650 g/L or from 500 to 650 g/L, in particular from 410 to 630 g/L or from 500 to 630 g/L and especially from 510 to 630 g/L.

it is, however, also possible to subject an aqueous solution of the 2'-FL raw material to the crystallization in step b), which has a concentrations of 2'-FL of above 630 g/L, in particular above 650 g/L.

Inducing conditions of controlled supersaturation at the given conditions ensures that the desired polymorph can be selectively crystallized from the aqueous solution of the 2'-FL raw material.

Controlled supersaturation means that during crystallization the degree of supersaturation does not exceed a value, where uncontrolled, i.e. spontaneous crystallization does occur. The degree of supersaturation is understood as the ratio of the actual concentration c of dissolved 2'-FL during crystallization to the equilibrium solubility c* of 2'-FL in water at the given conditions, i.e. the ratio c:c*. In particular the ratio c:c* will not exceed a value of 1.5:1, in particular a value of 1.3:1, more particular a value of 1.2:1, especially a value of 1.15:1. Apparently, supersaturation requires that the ratio c:c* exceeds the state of the thermodynamic equilibrium, i.e. the state where the ratio c:c* is 1, i.e. that c:c* has a value of more than 1:1. The value of more than 1:1 indicates e.g. a value of 1.00001:1, 1.0005:1, 1.0001:1, 1.0005: 1, 1.001:1 or 1.0002:1, in particular a value in the range of 1.00001 to 1.002:1. The equilibrium concentration c* of 2'-FL in water at a given temperature or pressure is known or can be determined by routine experiments. The actual concentration of dissolved 2'-FL in water can be calculated utilizing the concentration of 2'-FL in the aqueous solution, the amount of 2'-FL fed to the crystallization apparatus, the amount of water removed and the amount of crystallized 2'-FL. The actual concentration of the solution or suspension may also be determined experimentally, e.g. by ATR-FTIR (Attenuated Total Reflection Fourier Transform Infrared Spectroscopy) or by density measurement.

The concentration of dissolved 2'-FL and thus the degree of supersaturation is usually adjusted by removing water from the aqueous solution of the 2'-FL raw material, i.e. by increasing the concentration of 2'-FL under conditions of the crystallization, and/or by cooling, i.e. by decreasing the solubility of 2'-FL under conditions of crystallization, and in particular by evaporation or by a combination of both.

For achieving or maintaining conditions of supersaturation, water is preferably removed by evaporation. In particular, conditions of supersaturation are induced and maintained by evaporation of water or by combined evaporation/cooling. In other words, the crystallization is preferably carried out as an evaporation crystallization. i.e. the concentration of 2'-FL in the reaction vessel is increased under conditions of the crystallization by evaporation of water, which may of course be accompanied by cooling or where after evaporation of water the initially obtained aqueous suspension of the crystalline 2'-FL is cooled to increase the yield of crystallized 2'-FL.

Preferably, water is removed by evaporation under reduced pressure. Preferably, water is evaporated at pressures in the range from 10 to 900 mbar, in particular in the range from 50 to 800 mbar.

Preferably, evaporation is performed at a temperature of at least 20° C., in particular at least 25° C., more particularly at least 30° C., especially at least 35° C. Generally, the temperature will not exceed 105° C., in particular not exceed 100° C. or 95° C. In particular, the evaporation temperature will not exceed 62° C. or 60° C. The temperature, where evaporation is performed, will also depend on the type of polymorph produced. If it is desired to obtain polymorph A or polymorph B, the aqueous solution is usually concentrated at a temperature in the range from 20 to below 52° C., in particular in the range from 25 to 50° C., more particularly from 30 to 48° C., especially from 35 to 45° C. while for obtaining the anhydrate form II the aqueous solution of the 2'-FL raw material is usually concentrated at a temperature in the range from above 52 to 105° C., frequently from 52 to 100° C. or from 52 to 95° C., in particular from 52 to 65° C. or from 52 to 60° C.

Evaporation of water may be achieved by conventional means using any equipment which allows for removal of water by distillation. The type of apparatus will depend in a known manner from whether water is removed during pre-concentration or for inducing conditions of controlled supersaturation and also whether the crystallization is operated discontinuously, i.e. batch or semi-batch, or continuously.

For inducing conditions of supersaturation by evaporation of water in a batch or semi-batch operated crystallization a simple vessel may be used, where the necessary heat is transferred by a heating device, e.g. by a double jacket, by heating elements in the vessel, by an external pumping loop with a heat exchanger or by a combination of these apparatuses. If the crystallization is performed in a continuous manner, a continuously operating crystallization apparatus will be used for inducing conditions of supersaturation by evaporation of water, such as stirred tank vessels, stirred tank vessels with guiding pipe, forced circulation crystallizers (FC), draft tube baffle crystallizers (DTB) or Oslo crystallizers. The evaporators may be heated with conventional heating media such as heating oils or heating steam, including steam from a steam network or steam provided in the process of the present invention by vapor recompression.

Evaporation of water in the pre-concentration step may be achieved by conventional means using any equipment which allows for removal of water by distillation, such stirred tank vessels, thin film evaporators, falling film evaporator and helical tube evaporators. Preferably, evaporation of water in the pre-concentration step is achieved by means of a falling-film evaporator, preferably using heating steam obtained by mechanical vapor recompression. Mechanical vapor recompression allows for reducing the required amount of fresh steam, thereby reducing the overall costs. Vapor recompression is preferably achieved by one or more rotary compressors. Because of the moderate compression stroke of the vapor recompression and thus the limited temperature raise at the heating section falling film evaporators are preferably used, as they can be operated at a small temperature gradient. The falling film evaporator allows for a high evaporation rate at small circulation rates and low pressure drops. Thus, falling film evaporators allow for short residence times of the temperature sensible 2'-FL. Moreover the low pressure drop of falling film evaporators is beneficial for vapor recompression and thus for heat recovery. It is beneficial to connect several evaporators in series, because this allows for keeping the temperature difference between heating side and process side high, thereby allowing for small surfaces in the heat exchanger.

The amount of water removed is usually chosen such that at least at the beginning of the crystallization the concentration of dissolved 2'-FL in the aqueous medium present in the crystallization is in the range as given above and thus may vary from 400 to 750 g/L or from 500 to 750 g/L and in particular from 410 to 720 g/L or from 510 to 720 g/L, depending on the temperature during crystallization. As explained above, a concentration of dissolved 2'-FL of at most 650 g/L, in particular at most 630 g/L, e.g. in the range from 400 to 650 g/L and especially from 410 to 630 g/L, in the aqueous medium present during crystallization may be beneficial. However, concentrations of 2'-FL of above 630 g/L, in particular above 650 g/L in the aqueous medium present during crystallization may also be possible. It is also apparent that in a continuously operated crystallization the concentration of dissolved 2'-FL in the water present during crystallization is in the ranges given here throughout the crystallization.

For effecting crystallization, the controlled supersaturation is typically induced at a temperature of at least 0° C., in particular at least 10° C. or at least 20° C. The temperature, where the controlled supersaturation is induced, will typically not exceed 105° C. in particular not exceed 100° C. more particularly not exceed 95° C. or 90° C., especially not exceed 85° C. In order to avoid discoloration, the temperature will preferably not exceed 70° C., in particular 65° C. or 60° C. and is in particular below 60° C.

If controlled supersaturation is induced by a process which includes evaporation of water, hereinafter referred to as evaporation crystallization, the temperature where supersaturation is induced is typically at least 20° C., in particular at least 25° C., especially at least 30° C. or at least 35° C. Generally, the temperature will not exceed 105° C., in particular not exceed 100° C. more particularly not exceed 95° C. or 90° C., especially not exceed 85° C. In order to avoid discoloration of the mother liquor the crystallization temperature will preferably not exceed 70° C., in particular 65° C. or 60° C. and is in particular below 60° C. In particular, the supersaturation is induced at a temperature in the range from 0 to 95° C. or in the range from 0 to 60° C., more particularly in the range from 0 to 90° C. or in the range from 0 to below 60° C., especially in the range from 0 to 85° C. or in the range from 0 to 58° C. If controlled supersaturation is induced by evaporation crystallization, the supersaturation is preferably induced at a temperature in the range from 25 to 95° C. or in the range from 25 to 60° C., more preferably in the range from 30 to 90° C. or in the range from 30 to below 60° C. and especially in the range from 35 to 85° C. or in the range from 35 to 58° C.

If it is intended to produce polymorph B or A, respectively, by evaporation crystallization, the supersaturation is typically induced at a temperature in the range from 20 to 52° C., in particular in the range from 25 to 50° C., more particularly in the range from 30 to 48° C. especially in the range from 35 to 45° C. For production of the hydrate form II supersaturation is typically induced at a temperature in the range from above 52 to 105° C., in particular in the range from 52 to 100° C., especially in the range from 52 to 95° C. or from 52 to 90° C. or from 52 to 85° C. or from 52 to 60° C. or from 52 to below 60° C. or from 52 to 58° C.

If controlled supersaturation is induced by a process which does not include evaporation of water, e. g. where the temperature where supersaturation is induced by cooling, the temperature may be lower than the above given ranges and may be as low as 0° C. In this case the temperature, where crystallization is induced, is typically in the range from 0 to 60° C., in particular in the range from 0 to below 60° C., or in the range from 0 to 58° C. The temperature will of course depend on the desired polymorph form of 2'-FL.

The crystallization of 2'-FL is usually performed at ambient pressure or under reduced pressure, e.g. at a pressure in the range from 10 to 1020 mbar. The pressure will of course depend on the temperature and the concentration of the aqueous solution of the 2'-FL raw material. It may be beneficial to perform the crystallization of 2'-FL at reduced pressure in order to facilitate removal of water by evaporation during crystallization. Then, crystallization of 2'-FL is preferably carried out at a pressure in the range from 10 to 900 mbar, in particular from 20 to 800 mbar and especially from 30 to 700 mbar.

During crystallization the temperature may be further reduced and/or water may be further evaporated in order to drive crystallization to completion, in particular, if crystallization is performed batch-wise or in semi-batch procedures. Of course, the temperature will be in the above ranges, if crystallization of 2-FL' is performed continuously.

In order to achieve a control of supersaturation, measures are taken which favor crystallization and prevent kinetic inhibition of crystallization and thus excess oversaturation. Such measures are in particular performing the crystallization in the presence of solids, such as amorphous 2'-FL or in particular crystalline 2'-FL. It is also possible to use mixtures of amorphous and crystalline 2'-FL. If crystalline 2'-FL is used for this purpose, any crystalline form can be used. Other solids may also be used, including solid $CO_2$. It may also be possible to apply ultrasound in order to prevent kinetic inhibition of the crystallization. Of course measures which favor crystallization will be taken in particular, when the ratio c:c* does not exceed a value of 1.5:1, in particular not exceed a value of 1.3:1, more particular not exceed a value of 1.2:1, especially not exceed a value of 1.15:1.

According to one embodiment of the invention, seed crystals of 2'-FL are added, preferably but not necessarily seed crystals of the desired polymorph form. This measure is in particular taken, if the crystallization is conducted in a discontinuous manner. Then the amount of seed crystals will usually be in the range from 0.01 to 5% by weight, in particular in the range from 0.02 to 3% by weight or 0.02 to 1% by weight, with respect to pure 2'-FL in the aqueous solution subjected to crystallization in step b).

In order to perform the crystallization in the presence of crystalline 2'-FL, it is also possible to feed the aqueous solution to a suspension of crystalline 2'-FL in water under conditions of controlled supersaturation. In the aqueous suspension, the solid content is preferably in the range from 5 to 60% by weight, in particular from 10 to 45% by weight and especially from 20 to 40% by weight, based on the total weight of the suspension. Preferably, the concentration of dissolved 2'-FL in the aqueous phase of the suspension of 2'-FL under the conditions of supersaturation is preferably in the range from 400 to 750 g/L or from 500 to 750 g/L, in particular from 410 to 720 g/L or from 510 to 720 g/L, more particularly in the range from 400 to 650 g/L and especially from 410 to 630 g/L, depending on the temperature during crystallization and depending on which polymorph form is desired.

In a very preferred group of embodiments, the crystallization of step b) is carried out at a temperature in the range from 20 the 52° C., in particular in the range from 25 to 50° C., more particular in the range from 30 to 48° C. and especially in the range from 35 to 45° C. in the presence of solid 2'-fucosyllactose, in particular crystalline 2'-fucosyllactose (any of the known polymorphs of 2'-FL can be used), and where the crystallization is effected from an aqueous supersaturated solution under the conditions of controlled supersaturation as described herein, where the aqueous supersaturated solution has a concentration of dissolved 2'-fucosyllactose at least initially in the range from 410 to 630 g/L.

The crystallization of 2'-FL can be performed in any type of crystallization apparatus which can be utilized for a crystallization of an organic compound from an aqueous solution. Suitable crystallization apparatus include but are not limited to stirred tank crystallizers, stirred tank crystallizers with guiding pipe, stirred tank crystallizers with guiding pipe and optionally with means for classification of the crystals, so called draft tube crystallizers or draft tube baffle (DTB) crystallizers, forced circulation crystallizers optionally having means for crystal classification, such as Oslo-type crystallizers, induced forced circulation crystallizers optionally having means for crystal classification, and cooling-plate crystallizers. Preferred crystallizers are selected from the group of forced circulation crystallizers, draft tube crystallizers, draft tube baffled crystallizers, Oslo-type crystallizers and induced forced circulation crystallizers, with particular preference given to draft tube baffled crystallizers and induced forced circulation crystallizers.

As pointed out above, the method of the invention can be performed discontinuously, i.e. batch-wise, or as a semi-batch or continuously.

Batch-wise means that the aqueous solution of the 2'-FL raw material is charged to a crystallization vessel and conditions of controlled supersaturation are induced therein in order to effect crystallization of 2'-FL. Thereby 2'-FL is depleted from the solution and thus the concentration of 2'-FL decreases. In order to prevent kinetic inhibition of crystallization, solid matter, in particular amorphous or crystalline 2'-fucosyllactose and especially seed crystals of 2'-FL are preferably added. In order to maintain conditions of controlled supersaturation, water may be evaporated during crystallization or the temperature may be decreased during crystallization or both measures are taken. In particular solid matter, in particular amorphous or crystalline 2'-fucosyllactose (any of the known polymorphs of 2'-FL can be used) or mixtures of crystalline and amorphous 2'-FL and especially seed crystals of 2'-FL are added, when the ratio c:c* does not exceed a value of 1.5:1, in particular not exceed a value of 1.3:1, more particular not exceed a value of 1.2:1, especially not exceed a value of 1.15:1. Usually, the obtained aqueous suspension of the crystalline 2'-fucosyllactose is discharged from the crystallization vessel and subjected to a solid-liquid separation step, when the desired amount of 2'-fucosyllactose has been crystallized from the solution. Frequently, the batch-wise crystallization is carried out such that the suspension finally contains the solid crystalline 2'-FL in an amount from 5 to 55% by weight, in particular from 10 to 45%, especially 20 to 40% by weight, based on the weight of the suspension.

Semi-batch means that a portion of the aqueous solution of the 2'-FL raw material is charged to a crystallization vessel and conditions of controlled supersaturation are induced therein in order to effect crystallization of 2'-FL. In order to prevent kinetic inhibition of crystallization, solid matter, in particular amorphous or crystalline 2'-fucosyllactose (any of the known polymorphs of 2'-FL or mixtures of amorphous and crystalline 2'-FL can be used) and especially seed crystals of 2'-FL are preferably added. Then, further amounts of the aqueous solution of the 2'-FL raw material are fed to the crystallization apparatus and thus to the aqueous suspension of partially or completely crystallized 2'-FL. In order to maintain conditions of controlled supersaturation, water may be evaporated during crystallization or the temperature may be decreased during crystallization or both measures are taken. Usually, the obtained aqueous suspension of the crystalline 2'-fucosyllactose is discharged from the crystallization vessel and subjected to a solid-liquid separation step, when the desired amount of 2'-fucosyllactose has been crystallized from the solution. Frequently, the semi-batch-wise crystallization is carried out such that the suspension finally contains the solid crystalline 2'-FL in an amount from 5 to 55% by weight, in particular from 10 to 45%, especially 20 to 40% by weight, based on the weight of the suspension.

In another group of embodiments, the crystallization is performed continuously. For this, the aqueous solution of 2'-FL containing raw material provided in step a) is fed to a continuously operated crystallization apparatus, which contains an aqueous suspension of 2'-fucosyllactose crystals. In other words, the aqueous solution of 2'-FL is continuously fed to a continuously operated crystallization apparatus and the crystallized 2'-FL is continuously discharged from the crystallization apparatus.

In the continuously operated crystallization apparatus, conditions of controlled supersaturation are maintained throughout the crystallization. Preferably, conditions of controlled supersaturation are maintained by continuously removing defined amounts of water, preferably by evaporation, or by cooling or by combinations of these measures.

Frequently, the continuously operated crystallization apparatus is operated in such a manner that the conditions of controlled supersaturation are quasi-statical or almost quasi-statical. In particular, temperature variations are less than 5 K and/or pressure variations are less than 60 mbar.

Generally, the continuously operated crystallization apparatus contains an aqueous suspension of 2'-FL crystals. Preferably, the solids content of the aqueous suspension contained in the continuously operated crystallization apparatus, i.e. the amount of crystalline 2'-FL, is in the range from 5 to 60% by weight, in particular from 10 to 45% by weight, especially from 20 to 40% by weight, based on the total weight of the suspension contained in the continuously operated crystallization apparatus or in the active volume of the continuously operated crystallization apparatus. The active volume is understood as those parts of the crystallization apparatus, where the crystallization occurs, e.g. those parts which contain the free flowing aqueous suspension of 2'-FL crystals.

Frequently, step b) of the continuously operated crystallization apparatus comprises the following sub-steps:

b1) continuously feeding the aqueous solution of 2'-FL raw material to a continuously operated crystallization apparatus containing an aqueous suspension of crystalline 2'-FL, which preferably contains crystalline 2'-FL in an amount from 5 to 60% by weight, in particular from 10 to 45%, especially 20 to 40% by weight, based on the weight of the suspension;

b2) continuously removing water from the aqueous suspension of 2'-FL contained in the crystallization apparatus, preferably by evaporation, in particular by evaporation under reduced pressure;

b3) continuously removing the aqueous suspension of 2'-FL from the crystallization apparatus.

It has been found beneficial if the stream of the aqueous suspension of 2'-FL removed from the crystallizer in step b3) is split into two streams: A first stream is subjected to an isolation of crystalline 2'-FL, while the remainder is partly fed back to the crystallization apparatus together with fresh aqueous solution of 2'-FL raw material, provided in step b1). For this, a portion of the aqueous suspension of 2'-FL removed in step b3) is mixed with the aqueous solution of 2'-FL raw material of step b1) before it is fed to the crystallization apparatus. The thus obtained mixture is then fed back it into the crystallization apparatus. The volume ratio of the total stream removed from the crystallizer in step b3) to the first stream is subjected to an isolation of crystalline 2'-FL is at least 4:1, in particular at least 7:1, more particularly at least 10:1, e.g. from 4:1 to 200:1, or from 7:1 to 80:1 or from 10:1 to 60:1.

In order to remove water by evaporation the energy necessary for evaporation must be introduced into the crystallizer. This may be achieved by conventional heating elements. Preferably the evaporation heat is introduced into the crystallizer by feeding a heated stream of the aqueous solution of the 2'-FL raw material to the reactor. The heated stream of the aqueous solution of 2'-FL raw material which is fed into the reactor may be heated by any conventional heat exchanger. The heat exchanger may be operated with conventional heating media such as heating oils or heating steam, including steam from a steam network or steam provided in the process of the present invention by vapor recompression of water evaporated during crystallization or concentration of the aqueous solution of 2'-FL raw material. Preferably, the heated solution of 2'-FL raw material, which is fed into the crystallizer, is heated by using a forced circulation decompression evaporator, which is preferably heated by steam from vapor recompression of the water evaporated during crystallization or concentration of the aqueous solution of the 2'-FL raw material. Using a forced circulation decompression evaporator minimizes fouling on the heat exchanger surfaces.

The continuously operated crystallization apparatus is preferably a forced circulation crystallizer.

The crystallization of step b) is typically carried out such that at least 30%, in particular at least 40%, e.g. from 30 to 95%, in particular from 40 to 90% of the 2'-fucosyllactose initially contained in the aqueous solution which is subjected to the crystallization in step b) has been crystallized. A skilled person will immediately appreciate that a low percentage of crystallized 2'-fucosyllactose will result in a higher purity while a high percentage crystallized 2'-fucosyllactose will result in a lower purity of the obtained crystalline 2'-fucosyllactose.

In step b) a suspension of crystalline 2'-fucosyllactose in the aqueous mother liquor is obtained. In step c) the crystallized 2'-FL is separated from the aqueous mother liquor. For this, the suspension of crystallized 2'-FL in the aqueous mother liquor is subjected to solid/liquid separation. Suitable measures for the separation of solids from liquids include centrifugation, filtration, or washing towers. Means for centrifugation may include, but are not limited to, pusher centrifuges, worm screen centrifuges, peeler centrifuges and decanters. Means for filtration may include, but are not limited to, rotary pressure filters, belt filters, suction filters, chamber filters and chamber filter presses. Suitable washing towers may include, but are not limited to, gravity wash columns, mechanical wash columns, hydraulic wash columns and piston type wash columns. Preferably, solid/liquid separation is performed by centrifugation, in particular by utilizing a pusher centrifuge or a worm screen centrifuge, because thereby low residual moisture in the obtained solid can be achieved, which is frequently less than 10% by weight, e.g. from 1 to 8% by weight.

The solid/liquid separation may be performed stepwise or is performed continuously.

The obtained solid may be washed in order to remove adherent mother liquor, e.g. by cold solvent such as water or a saturated aqueous solution of pure 2'-FL. A suitable solvent, which can be utilized for washing of solid 2'-FL, may also be a mixture of water and a non-solvent for 2'-FL. Typical non-solvents are $C_1$-$C_4$-alkanols, such as methanol, ethanol, n-propanol or n-butanol, and acetic acid. A suitable solvent, which can be utilized for washing of solid 2'-FL, may also be a mother liquor of a subsequent crystallization step, if the crystallization is performed in more than one crystallization stages. A suitable solvent, which can be utilized for washing of solid 2'-FL, may also be a mixture of water and a non-solvent for 2'-FL, i.e. a mixture of non-solvent and mother liquor of a subsequent crystallization step, if the crystallization is performed in more than one crystallization stages. Washing may be performed e.g. by spraying the solid crystalline 2'-FL with the cold solvent followed by a further liquid/solid separation or by suspending solid crystalline 2'-FL in the cold solvent followed by a further liquid/solid separation. The washing may be performed in a single step or by multiple washing steps, e.g. by 2, 3 or more steps. If the washing is performed by multiple washing steps, the washing steps may be operated concurrently or preferably countercurrently.

In order to drive crystallization to completion and to increase the yield of crystalline 2'-fucosyllactose, it is possible to add a water miscible organic solvent to the suspension of 2'-fucosyllactose in the mother liquor prior to step b), when the crystallization is almost complete. In this context, almost complete is preferably understood that at least 80%, in particular at least 90% of the 2'-fucosyllactose has been crystallized, calculated on the basis of the amount of 2'-fucosyllactose, which can theoretically crystallize from the solution in step b) under the conditions of the crystallization chosen in step b). Typically, the organic solvent will only be added, if at least 30%, in particular at least 40%, e.g. from 30 to 95%, in particular from 40 to 90% of the 2'-fucosyllactose initially contained in the aqueous solution which subjected is subjected to the crystallization in step b) has been crystallized. Suitable water-miscible organic solvents will be completely miscible with deionized water at 20° C. and 1 bar. Examples of suitable organic solvents include $C_1$-$C_4$-alkanols and $C_1$-$C_4$-alkanoic acids, in particular ethanol, acetic acid and/or propionic acid, and mixtures thereof. The amount of organic solvent is frequently chosen such that the weight ratio of organic solvent to water is at least 1:1, e.g. in the range from 1:1 to 10:1. Surprisingly, the addition of organic solvents results in a higher purity of the obtained 2'-fucosyllactose.

The crystallization of 2'-FL will frequently comprise a single crystallization step, as a single crystallization will generally ensure a purity of 2'-FL, which is sufficient for most purposes. However, the crystallization of 2'-FL may comprise two or more crystallization steps, 2 or 3 subsequent crystallization steps or stages. The further crystallization stages may involve a re-crystallization of the crystalline material obtained in the first crystallization stage. In this case, the further crystallization stages may be performed in accordance with the method described above involving crystallization under conditions of controlled supersaturation and are useful to further increase the purity of the desired 2'FL. It is also possible to subject the mother liquor obtained in the first crystallization stage to a second crystallization stage, in order to increase the yield of 2'-fucosyllactose. In this case, it is possible to mix the mother liquor with a portion of the aqueous solution of the 2'-fucosyllactose raw material and subject the mixture to the crystallization.

In order to increase the yield of crystalline 2'-fucosyllactose, a portion or the complete amount of the mother liquor obtained in step c) may be subjected to a crystallization of 2'-fucosyllactose by inducing conditions of a controlled supersaturation in the mother liquor. For this, the mother liquor may be subjected to a further crystallization, preferably according to the method as described herein. However, it is also possible to mix at least a portion of the mother liquor with the solution of the 2'-fucosyllactose raw material prior to carrying out step b) and then subject the mixture to a further crystallization of 2'-fucosyllactose according to the method as described herein.

According to a first preferred group of embodiments the multi-stage crystallization method comprises a first crystallization step and a second crystallization step, and optionally one or more, e.g. 1 or 2 further crystallization steps, where at least in the second crystallization step and preferably also in the first crystallization step the crystallization of 2'-fucosyllactose is effected by inducing conditions of a controlled supersaturation in the solution by the method as described herein. In this preferred group of embodiments, the aqueous solution of the 2'-fucosyllactose raw material provided in step a) is subjected to the crystallization of the second crystallization step. From this second crystallization step, an aqueous suspension of the crystalline 2'-fucosyllactose in the mother liquor is obtained which is then subjected to a solid-liquid separation according to step c) whereby crystalline 2'-fucosyllactose and a mother liquor is obtained. This mother liquor is then fed into the first crystallization step. The first crystallization step may be carried out as described herein for step b) or according to a crystallization according to the prior art. Preferably, the first crystallization step is carried out according to step b) as described herein. The first crystallization step results in an additional amount of crystalline 2'-fucosyllactose. Frequently, the purity of the crystalline 2'-fucosyllactose obtained in the first crystallization step is somewhat lower than the purity of the crystalline 2'-fucosyllactose obtained in the second crystallization step. The crystalline 2'-fucosyllactose obtained in the first crystallization step may be used as such. However, it may also be dissolved in the aqueous solution of the 2'-fucosyllactose raw material provided in step a), and the thus obtained solution is subjected to the crystallization of the second crystallization step.

According to a second group of embodiments of a multi-stage crystallization method, the aqueous solution of the 2'-FL raw material provided in step a) is fed to a crystallization stage (1), which is operated batch-wise or continuously as described above. The crystalline 2'-FL obtained in this stage (1) is then dissolved in water and the obtained solution is subjected to a subsequent crystallization step (2), where a purified crystalline 2'-FL and a further mother liquor is obtained. The mother liquor of the subsequent crystallization step (2) may be mixed with water and the mixture is then used for dissolving the crystalline 2'-FL obtained in crystallization step (1). The crystalline 2'-FL obtained in stage (2) may be subjected to one or more, e.g. to 1 or 2 further crystallization stages (3) and (4), respectively. For example, the mother liquor of the subsequent crystallization step (n+1) is mixed with water and this mixture is used for dissolving the crystalline 2'-FL obtained in crystallization step (n), where n indicates the respective crystallization step. The mother liquor of the first crystallization stage may be discarded.

According to a combination of the first and the second group of embodiments the mother liquor of the first crystallization stage is subjected to a further crystallization stage, also termed stripping stage, to obtain a residual mother liquor, which is discarded, and crystalline 2'-FL of lower purity. The crystalline 2'-FL of lower purity obtained in said crystallization stage may be dissolved, e.g. in the aqueous solution of 2'-FL provided in step a) to obtain a more concentrated solution, which is fed into the crystallization step (1). The crystalline 2'-FL obtained in said crystallization from the mother liquor of step (1) may also be dissolved in a mixture of water and the mother liquor obtained in crystallization step (1) and combined with the aqueous solution of 2'-FL provided in step a) to obtain a more concentrated solution, which is fed into the crystallization step (1).

According to the invention, at least crystallization stage (1) of the second group of embodiments and of the combination of the second and the first group of embodiments is performed in accordance with the method described above, which involves crystallization under conditions of controlled supersaturation. If the crystallization stage is followed by the crystallization stage (2), also crystallization stage (2) is preferably performed in accordance with the method described above, which involves crystallization under conditions of controlled supersaturation.

The method according to the invention is described in detail hereinafter with reference to FIGS. 1 to 9. The figures shown serve for illustration and are not intended to restrict the invention thereto.

Figure 1:
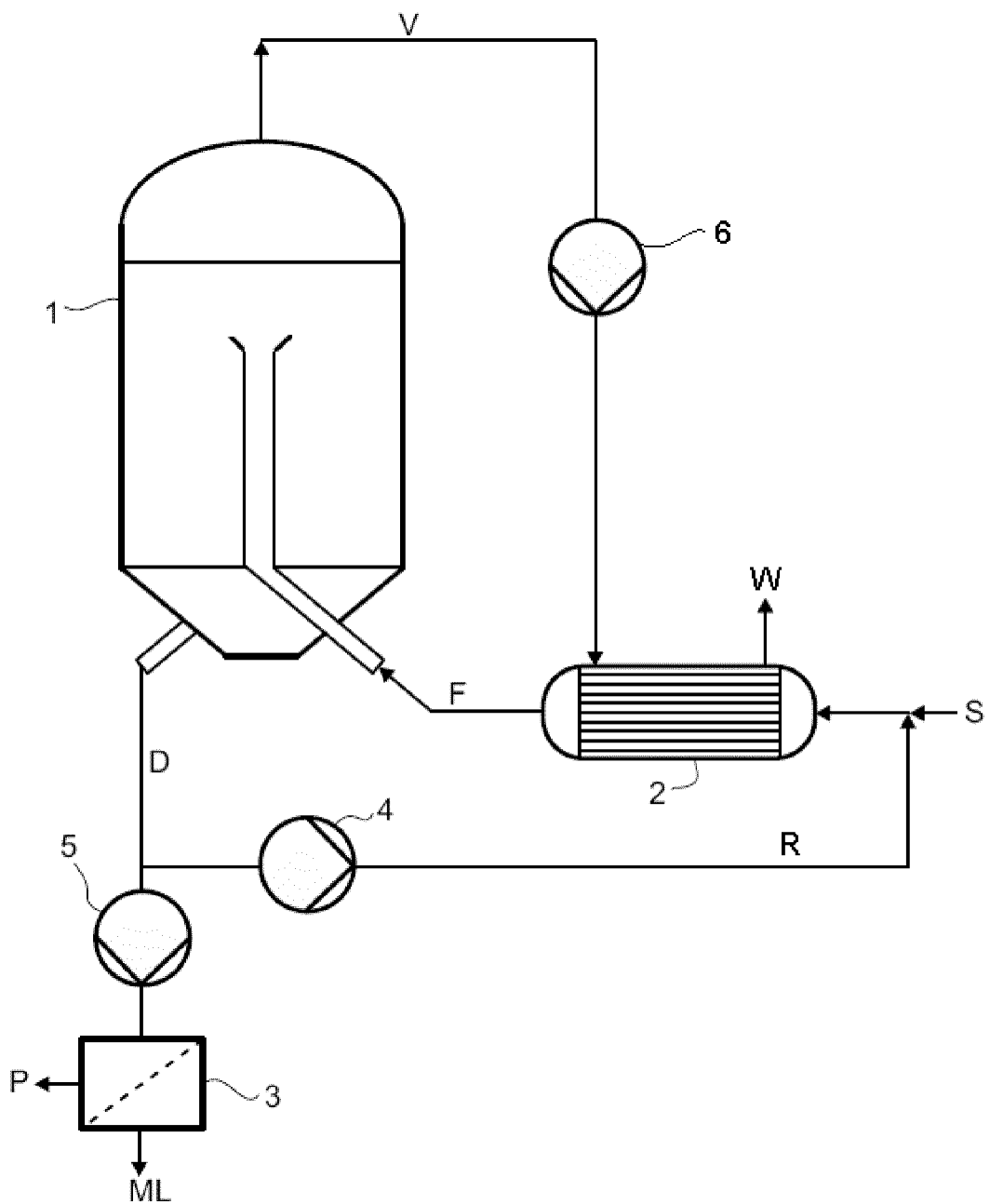
FIG. 1 shows a basic flow chart of the process according to the invention.

In the figures, the following reference symbols are used:
C crystalline phase/crystals
CR Crystallization
D Discharge
DU Dilution unit
F Feed
L Liquor
ML mother liquor
MLR recycled mother liquor
P Product
R recycled suspension
RL residual liquor
S fresh solution
SLS solid/liquid separation
V Vapor
W condensed vapor (liquid water)
WL wash liquid
i index for the stage
1 Crystallizer
2 heat exchanger
3 Separator
4 circulation pump
5 concentrate pump
6 compressor for vapor
10 Inlet
11 slurry withdrawal
12 suspension outlet
13 liquid withdrawal/overflow
14 draft tube
15 Demister
16 vapor outlet
17 settling zone
18 Agitator 19 Inducer
20 vapor separation zone
21 active volume As illustrated in FIG. 1, a fresh stream S containing an aqueous solution of the 2'-FL raw material is combined with a recycle stream R and heated in a heat exchanger 2 to a temperature of at least 40° C., for example in the range of from 40° C. to 95° C., to give an aqueous solution of the 2'-FL raw material as feed stream F. The heat exchanger 2 can be arranged either horizontally or vertically depending on the specific requirements. The feed F is then fed to a continuously operated crystallizer 1. The crystallizer 1 contains as active volume an aqueous supersaturated suspension of 2'-FL with a content of solid 2'-FL of 5% to 50% by weight, for example from 20% to 40% by weight, based on the weight of the suspension. Feeding the under-saturated aqueous solution of 2'-FL raw material F into the active volume and removing water at the same time, the concentration of 2'-FL in the over-saturated suspension, i.e. in the active volume of the crystallizer 1 is levelled off. The controlled supersaturation of 2'-FL in the aqueous suspension is effected at a temperature of at least 25° C., for example in the range of from 30° C. to 95° C., depending from the desired polymorph of 2'-FL, and at reduced pressure, for example in the range of from 20 mbar to 800 mbar.

Water is removed from the aqueous suspension of 2'-FL by evaporation, the water vapor V being withdrawn at the head from the crystallizer 1. The vapor V can be further conveyed via a compressor 6 to heat the heat exchanger 2, conducted for example in countercurrent to the feed F to be heated, and leaving the heat exchanger 2 as condensate W.

A discharge D of the slurry containing crystalline 2'-FL is removed at the lower end from the crystallizer 1. From the discharge D, a partial stream is taken as recycle stream R and conveyed via a recycling pump 4 to be mixed with the fresh stream S before, on or after entry into the heat exchanger 2. The discharge D will be portioned in such a way that the mass ratio of the recycle stream R to the fresh stream S is preferably greater than 5, in particular greater than 10, greater than 20, for example in the range of from 40:1 to 60:1.

The other part of the discharge D is routed by means of a concentrate pump 5 to a separator 3. In the separator 3, the slurry D is separated to obtain mother liquor ML and crystalline 2'-FL as product P. If desired, the mother liquor ML can be recycled to the inventive process or a preceding stage.

Alternatively, a discharge D of the slurry containing crystalline 2'-FL is removed on the side of the lower end from the crystallizer 1. The discharge D is routed by means of a concentrate pump 5 to a separator 3. In the separator 3, the slurry D is separated to obtain mother liquor ML and crystalline 2'-FL as product P. If desired, the mother liquor ML can be recycled to the inventive process or a preceding stage. A second discharge is removed as recycle stream R in the center part of the lower end from the crystallizer 1. The recycle stream R is conveyed via a recycling pump 4 to be mixed with the fresh stream S before, on or after entry into the heat exchanger 2. The mass ratio of the recycle stream R to the fresh stream S is greater than 5, in particular greater than 10, greater than 20, for example in the range of from 40:1 to 60:1. This alternative withdrawal of two different slurries can prove in particular advantageous if the slurry D taken at the side of the crystallizer is thicker or contains crystals of a different size distribution than the slurry R taken at the bottom of the crystallizer 1.

The crystallization may be preferably effected in a continuously operated crystallizer, for example a forced circulation crystallizer, a draft tube crystallizer or a draft tube baffled crystallizer, or in particular in an induced forced circulation crystallizer.

Figure 2:
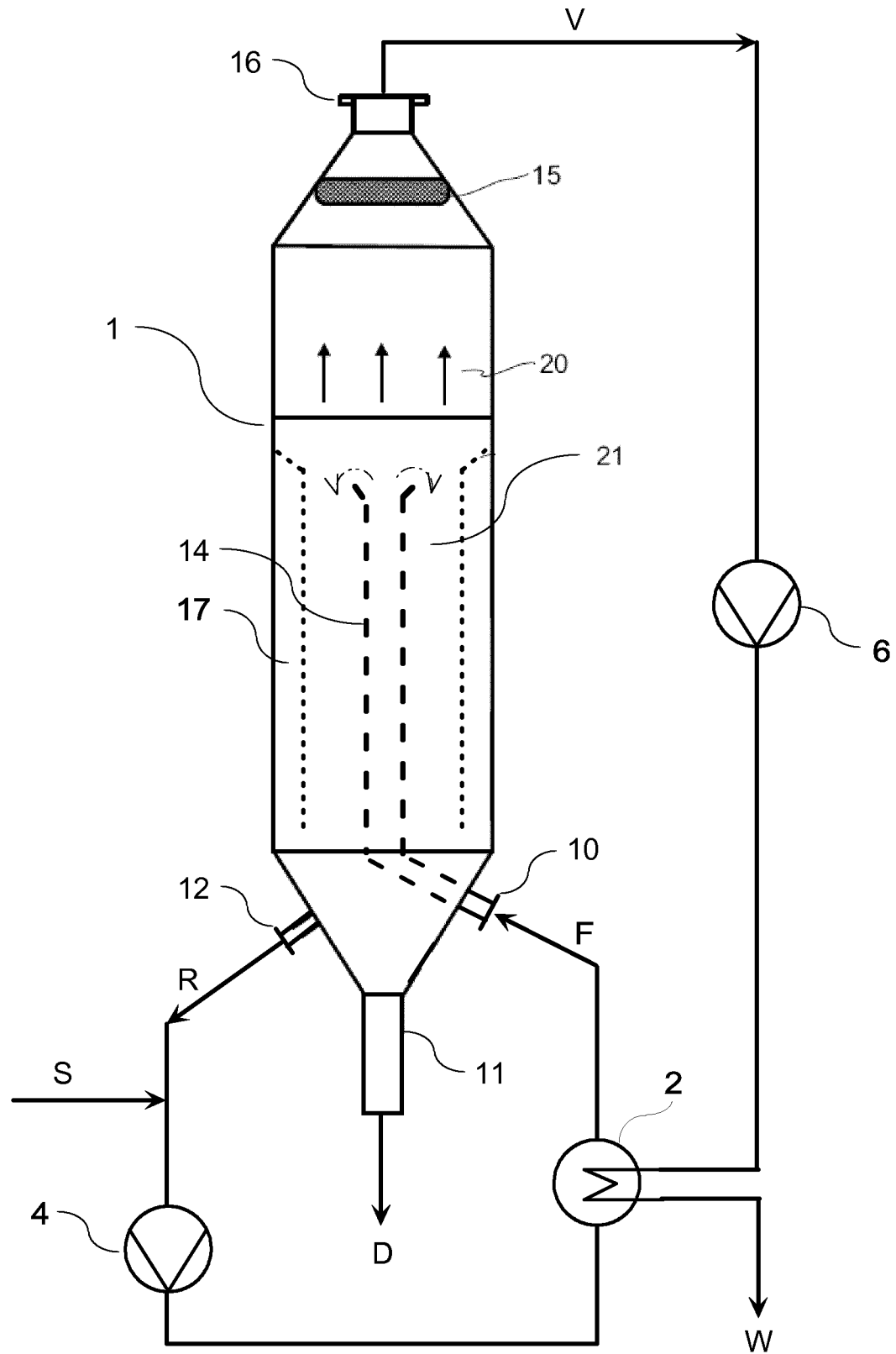
FIG. 2 shows one embodiment of a forced circulation crystallizer.

FIG. 2 shows a draft tube crystallizer. Superheated aqueous solution of the 2'-FL raw material F is fed to the crystallizer 1 via an inlet 10, flows upward through a draft tube 14 and returns downward along the outer side of the draft tube 14.

Water evaporated from the suspension in the active volume 21 rises as vapor V to the head of the crystallizer 1. The vapor V passes a vapor separation zone 20 and a demister 15 to remove liquid droplets and leaves the crystallizer 1 via a vapor outlet 16. The vapor V is further conveyed via a compressor 6 to heat the heat exchanger 2, conducted for example in countercurrent to the feed F to be heated, and leaving the heat exchanger 2 as condensate W. Around the active volume 21, a settling zone 17 may be arranged. Via a suspension outlet 12 in the lower region of the active volume 21, suspension R is removed and combined with the fresh solution S. The combined stream of R and S is recycled via a circulation pump 4 through a heat exchanger 2 as feed F into the crystallizer. The circulation pump 4 provides for the necessary agitation of the suspension mixed with the incoming solution F and effects the circulation of the suspension within the active volume 21.

Via a slurry withdrawal 11 situated at the bottom of the crystallizer 1 below the active volume 21, slurry D is removed from the crystallizer 1. The withdrawn slurry D contains the desired crystalline 2'-FL.

Figure 3:
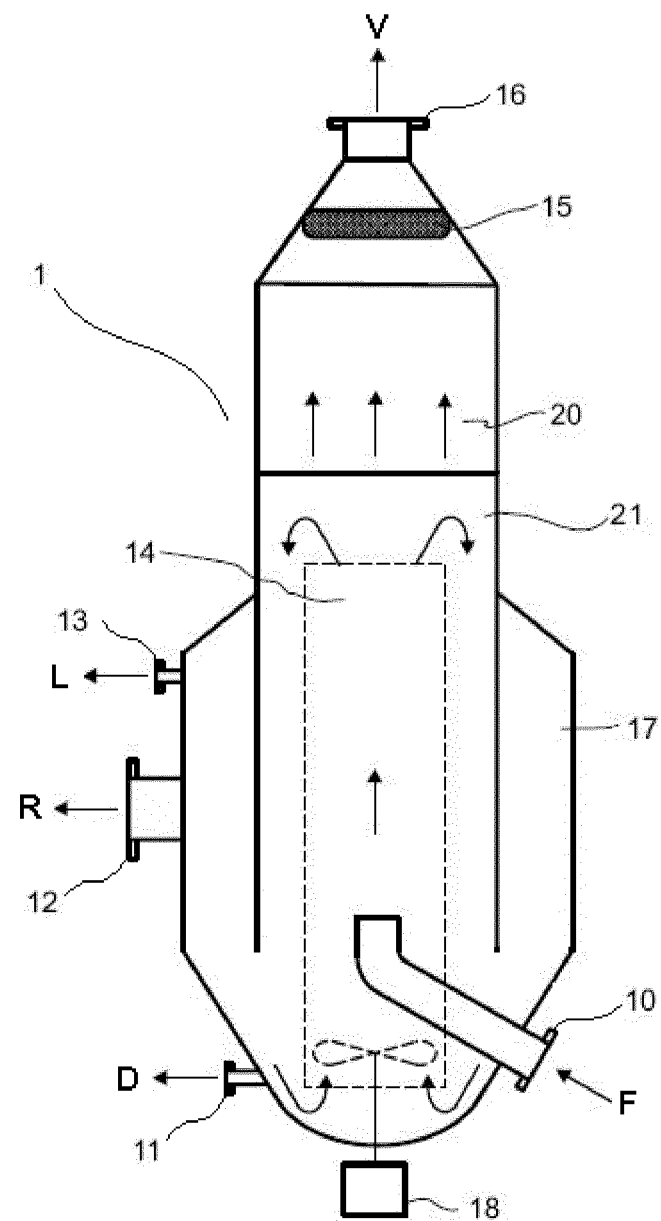
FIG. 3 shows another embodiment of a forced circulation crystallizer, in this case a draft baffle crystallizer.

FIG. 3 shows a draft tube baffled crystallizer with forced circulation. Superheated aqueous solution of 2'-FL raw material F is fed to the crystallizer 1 via an inlet 10, flows upward through a draft tube 14 and returns downward along the outer side of the draft tube 14. A bottom entry agitator 18 provides for the necessary agitation of the suspension mixed with the incoming solution F at moderate energy consumption and effects the circulation of the suspension within the active volume 21.

Water evaporated from the suspension in the active volume 21 rises as vapor V to the head of the crystallizer 1. The vapor V passes a vapor separation zone 20 and a demister 15 to remove liquid droplets and leaves the crystallizer 1 via a vapor outlet 16.

Peripheral to the active volume 21, a settling zone 17 is arranged by means of baffles. In the settling zone 17, excess mother liquor L and/or fines can be withdrawn for further processing at an overflow 13 in the upper region of the settling zone 17. This basically clear liquor L can be recycled to the process to regulate the temperature and/or the concentration of the solution of 2'-FL at any stage.

Via a suspension outlet 12 in the lower region of the settling zone 12, suspension R is removed and recycled to be mixed with the fresh feed stream S.

Via a slurry withdrawal 11 situated below the settling zone 12, slurry D is removed from the crystallizer 1. The withdrawn slurry D contains the desired crystalline 2'-FL as product P.

Figure 4:
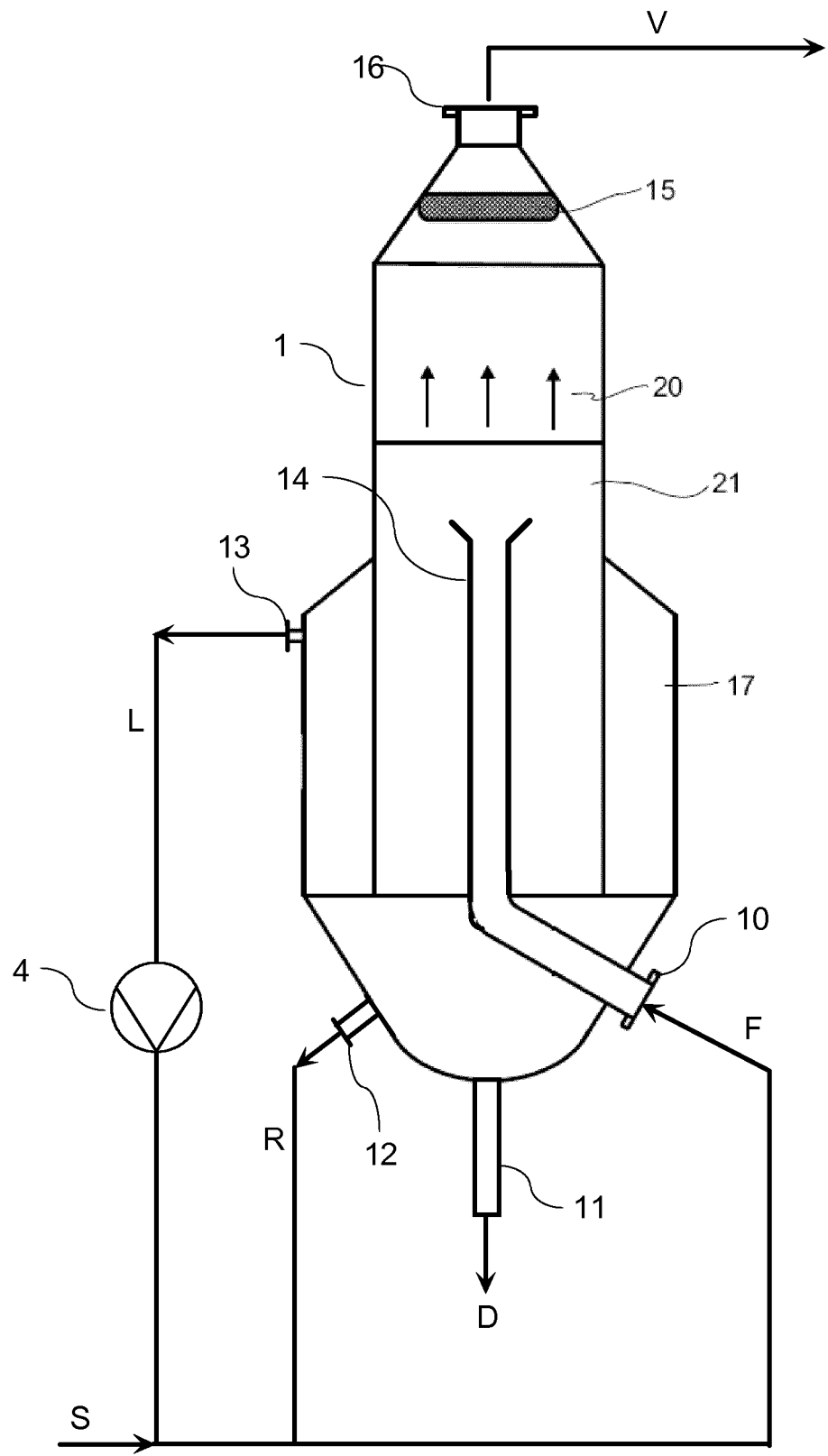
FIG. 4 shows an embodiment of induced forced circulation crystallizer.

The induced forced circulation crystallizer shown in FIG. 4 operates similarly to the forced circulation crystallizers shown in FIGS. 2 and 3 as explained above. Different to the embodiment shown in FIG. 3, the induced forced circulation crystallizer works without any internal agitation device.

Superheated aqueous solution of 2'-FL raw material F is fed to the crystallizer 1 via an inlet 10, flows upward through a draft tube 14 and returns downward along the outer side of the draft tube 14. Water evaporated from the suspension in the active volume 21 rises as vapor V to the head of the crystallizer 1. The vapor V passes a vapor separation zone 20 and a demister 15 to remove liquid droplets and leaves the crystallizer 1 via a vapor outlet 16.

Peripherical to the active volume 21, a settling zone 17 is arranged. Liquor L is withdrawn at a liquid withdrawal 13 in the upper region of the settling zone 17. This basically clear liquor L is recycled via the circulation pump 4. Via a suspension outlet 12 below the settling zone 12, suspension R is removed and combined with the clear liquor L in an external circuit. Fresh solution S is fed to the recycled stream L before, simultaneously or after combination with stream R. The combined recycled stream is heated in a heat exchanger (not shown in the figure) and fed to the crystallizer 1 as feed F. Analogously to the embodiment shown in FIG. 2, the vapor V may be used to heat the heat exchanger 2.

The throughput of the circulation pump 4 provides for the syphoning of the recycled suspension R and the necessary agitation of the suspension within the active volume 21. No further agitation devices are required, so that the crystals in the suspension are treated with the least possible strain.

Via a slurry withdrawal 11 situated at the bottom of the crystallizer 1 below the active volume 21 and below the settling zone 12, slurry D is removed from the crystallizer 1. The withdrawn slurry D contains the desired crystalline 2'-FL as product P.

Figure 5:
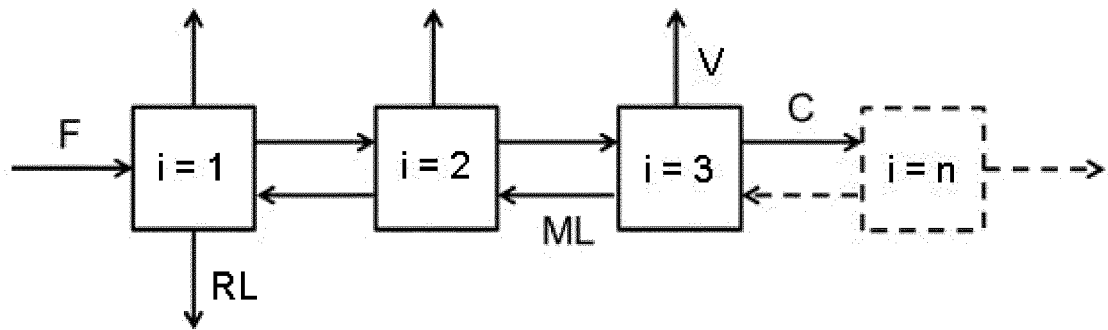
FIG. 5 shows a block diagram of an embodiment of a multi-stage process according to the invention.

In the multi-stage process according to FIG. 5, the crystallization is performed in n stages. It should be noted that stages 3 to n are optional stages. A feed F is introduced into a first crystallization stage (i=1). Solvent is removed from the first crystallization e.g. by way of evaporation. The suspension is separated into residual liquor RL and a first crystalline phase $C_1$. The first crystalline phase $C_1$ is passed into a second crystallization stage (i=2). Mother liquor from the second crystallization stage (i=2) is recycled into the first crystallization stage (i=1), e.g. by mixing it with water and using the mixture for dissolving the crystalline phase $C_1$ obtained in the first crystallization stage. In each crystallization stage (i=2 to n), water is removed, e.g. by withdrawing it in the form of solvent vapor V and the suspension is separated into mother liquor ML and a crystalline phase C. The crystalline phase from each crystallization stage (i) is passed into the following crystallization stage (i+1). Mother liquor from each crystallization stage (i) is recycled into the previous crystallization stage (i−1), for example by mixing it with water and utilizing the mixture for dissolving the crystalline 2'-FL from the previous crystallization stage. A crystalline phase containing the desired 2'-FL crystals is withdrawn from the last stage n. The number of stages n depends on the desired quality of the crystals in respect of form, purity, flow characteristics and storage properties.

Figure 6:
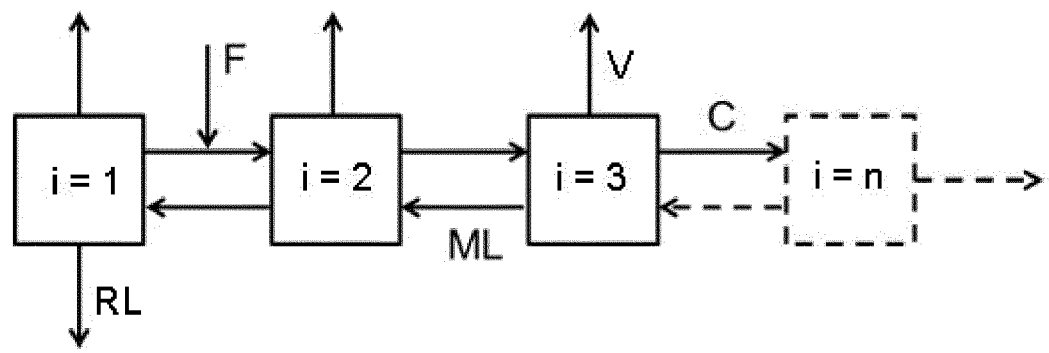
FIG. 6 shows a block diagram of a second group of embodiments of a multi-stage process according to the invention.

In the multi-stage process according to FIG. 6, the crystallization is performed in n stages, the first stage (i=1) being a stripping section. It should be noted that stages 3 to n are optional stages. The flow is similar to the flow described in FIG. 5, but feed F is introduced between the stripping stage (i=1) and the second crystallization stage (i=2). In general, the process according to FIG. 6 gives higher yields of the desired product.

Figure 7:
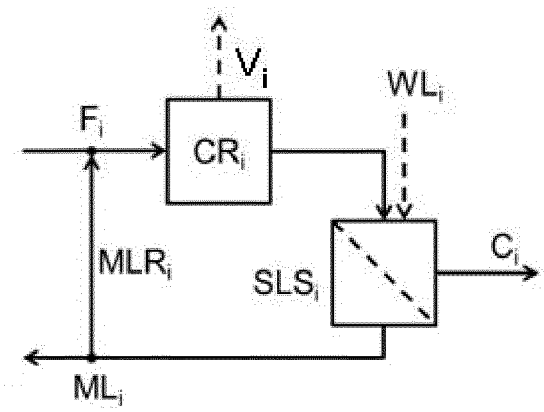
FIG. 7 shows schematically one crystallization stage according to the invention.

A crystallization stage (i) according to FIG. 7 comprises an apparatus each for crystallization $CR_i$ and for solid/liquid separation $SLS_i$. Apparatuses employed for the crystallization $CR_i$ are in general crystallizers suitable for crystalline suspensions such as stirred tank reactors, e.g. Swenson type crystallizers, forced circulation crystallizers, e.g. Oslo type reactors, draft tube reactors, draft tube baffled crystallizer (see FIG. 3), or induced forced circulation crystallizer (see FIG. 4). Apparatuses employed for the solid/liquid separation $SLS_i$ are in general centrifuges, decanters, filters, filter presses, or washing towers.

The feed $F_i$ for each stage (i) comprises suspension containing the crystalline phase $C_{i-1}$ from the previous stage (i-1) and/or fresh feed F, respectively, as well as recycled mother liquor $MLR_i$. Distillate is withdrawn from the crystallization $CR_i$ in the form of solvent vapor $V_i$. Subsequently, the suspension is separated in the solid/liquid separation $SLS_i$ into mother liquor $ML_i$ and a crystalline phase $C_i$. The crystalline phase $C_i$ from each crystallization stage (i) can be passed as feed $F_{i+1}$ into the following crystallization stage (i+1) or be withdrawn as product, respectively. One portion of mother liquor $ML_i$ from each crystallization stage (i) is recycled into the same stage as $MLR_i$. The rest of mother liquor $ML_i$ from each crystallization stage (i) can be recycled into the previous crystallization stage (i−1) or be withdrawn, respectively.

To enhance the purity of the product 2'-FL, washing liquid $WL_i$ can additionally be employed in the solid/liquid separation $SLS_i$. As washing liquid $WL_i$ cold water or cold mother liquor of a subsequent crystallization stage (i+1) is preferably used.

Figure 8:
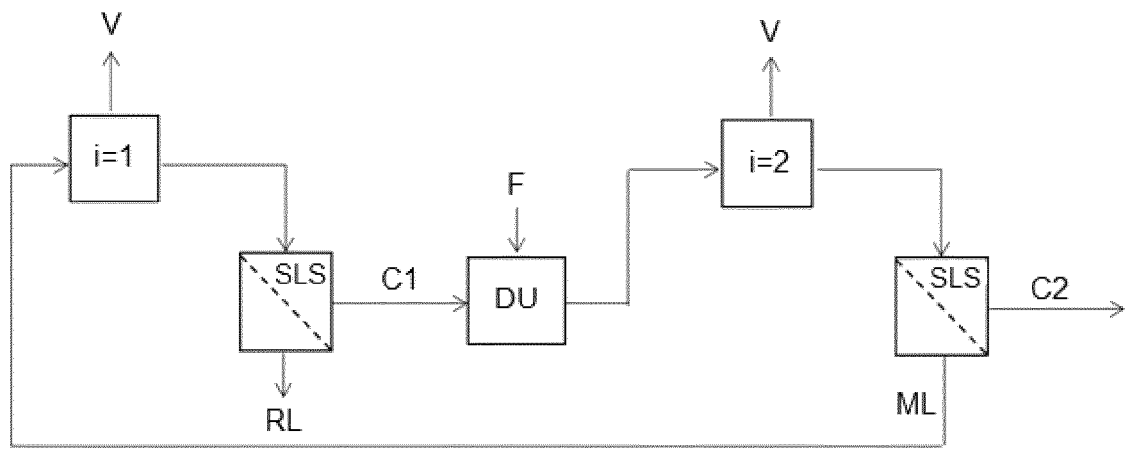
FIG. 8 shows schematically a two stage crystallization process according to the first group of embodiments of the invention.

In FIG. 8, a two stage process similar to FIG. 6 is depicted. The feed F is introduced between the stripping stage (i=1) and the second crystallization stage (i=2) into a dilution unit DU, where the crystalline 2'-fucosyllactose C1 obtained in the first crystallization stage is dissolved in the feed, i.e. in the aqueous solution of the 2'-fucosyllactose raw material. Water is removed from the second crystallization stage e.g. as vapor V by way of evaporation. Thereby a suspension of 2'-fucosyllactose in the mother liquor is obtained, which is subjected to a solid-liquid separation SLS2 to obtain a mother liquor ML and the purified crystalline 2'-fucosyllactose C2. The mother liquor from the second crystallization stage (i=2) is recycled into the first crystallization stage (i=1). Water is removed from the first crystallization stage e.g. as vapor V by way of evaporation. Thereby a suspension of 2'-fucosyllactose in a mother liquor is obtained, which is subjected to a solid-liquid separation SLS1 to obtain a residual liquor RL, which is discarded, and the crystalline 2'-fucosyllactose C1.

Figure 9:
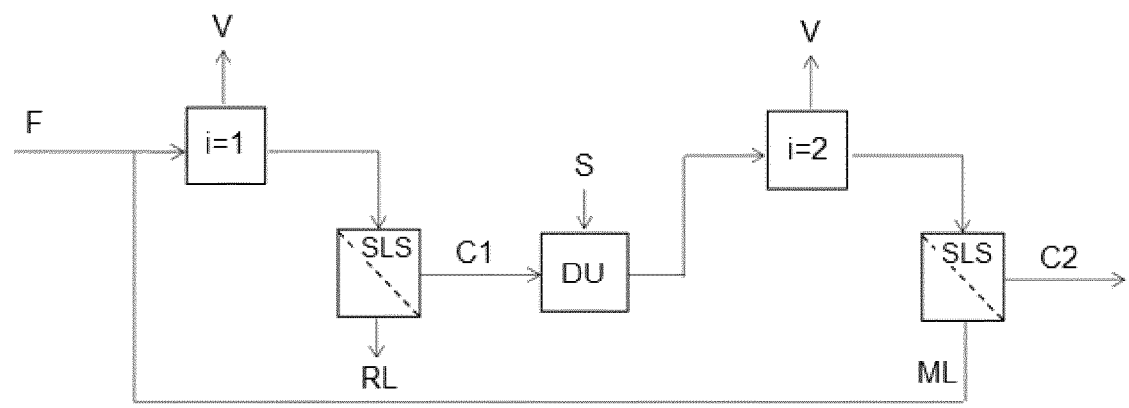
FIG. 9 shows schematically a two stage crystallization process according to the second group of embodiments of the invention.

In FIG. 9, a two stage process similar to FIG. 5 is depicted. The feed F, i.e. the aqueous solution of the 2'-fucosyllactose raw material, is introduced into the first crystallization stage (i=1). Water is removed from the first crystallization stage e.g. as vapor V by way of evaporation. Thereby a suspension of 2'-fucosyllactose in the mother liquor is obtained, which is subjected to a solid-liquid separation SLS1 to obtain a residual liquor RL, which is discarded, and a purified crystalline 2'-fucosyllactose C1. The crystalline 2'-fucosyllactose C1 is dissolved in solvent S (water or in further feed) in a dilution unit DU. The thus obtained solution is passed into a second crystallization stage (i=2). Water is removed from the second crystallization stage e.g. as vapor V by way of evaporation. Thereby a suspension of 2'-fucosyllactose in the mother liquor is obtained, which is subjected to a solid-liquid separation SLS2 to obtain a mother liquor ML and the purified crystalline 2'-fucosyllactose C2. Mother liquor ML from the second crystallization stage (i=2) is recycled into the first crystallization stage (i=1), e.g. by mixing it with the feed F.

Abbreviations:
2'-FL: 2'-O-fucosyllactose
DiFL: difucosyllactose
b.w.: by weight
rpm: rotations per minute
RT: Room temperature, i.e. about 22° C.
Analytics:
HPLC:
Column: Spherisorb NH2 column (amine modified silica: particle size 3 μm, pore size 80 Å) length 250 mm, internal diameter 4.5 mm (Waters Corporation)
Eluent: acetonitrile/water 82.5/17.5 v/v
Detection: RID
Parameters: flow rate 1.3 ml/min, T=35° C., pressure 112 bar, 5 μl injection volume
Determination of water: The concentration of water was determined by Karl-Fischer titration.
Dry matter content was determined by drying 2 g of the sample at 130° C. for 2 hours
Filter cake resistance was calculated based on the measured volume flow of the filtrate in the pressure nutsche, the applied pressure and the filter area.
Determination of crystalline form: Powder X-Ray Diffraction (PXRD)
X-ray diffraction patterns were recorded with a Panalytical X'Pert Pro diffractometer (manufacturer: Panalytical) in reflection geometry (Bragg-Brantano) in the range from 2θ=3°-40° with increments of e.g. 0.017° and measurement time of 20 s/step using Cu-Kα radiation (1.54178 Å) at 25° C. The tube voltage was 45 kV and current 40 mA. The sample was placed in a silicon single crystal sample holder of 0.2 mm depth and flattened.

CRYSTALLIZATION EXAMPLES

In examples 1 to 3 an aqueous solution of a 2'-FL raw material was used, which was obtained by fermentation and subsequent downstream processing including passing the fermentation broth through a bed of an ion exchange resin and concentration of the thus treated broth to a solids content of 61.1% by weight was used. The aqueous solution contained 52.5% by weight of 2'-FL and 8.6% by weight of mono- and oligosaccharides including lactose, DiFL and fucosyllactulose.

Example 1

In a reaction flask equipped with a distillation bridge and a stirrer 100 g of the aqueous solution of the 2'-FL raw material was heated by means of a water bath to 50° C. (bath temperature). At a pressure of 30 mbar 19.42 g of water were distilled off resulting in a syrup containing 65% by weight of 2'-FL. The weight ratio of product (2'-FL) to water in the obtained syrup was 2.74:1. The vessel was expanded to ambient pressure and the resulting viscous solution was allowed to cool to 45° C. (bath temperature) and seeded with 0.05 g of crystalline Form II of 2'-FL obtained from a previous run. The mixture was stirred at 45° C. (bath temperature) for further 4 h, allowed to cool to RT and stirred for further 16 h. The thus obtained thick suspension was warmed to 35° C. (bath temperature) and stirred for 2 h at 35° C. at ambient pressure. The warm suspension was filtered through a heated suction filter (35° C.) and the filter cake was washed 4 times with each 10 ml of ethanol/water (80/20 w/w) and thereafter dried at 40° C. and 0.8 mbar for 12 h. Thereby, 38.9 g of crystalline material (yield 70.5%) having the following composition was obtained:

Composition (HPLC): 95.1% 2'-FL, 0.2% lactose, 0.3% fucosyllactulose, 0.9% DiFL. The obtained crystalline material contained 3.3% by weight of water as determined by Karl-Fischer titration.
In the obtained crystalline material 2'-FL was present essentially as form A, as determined by PXRD.

Example 2

In a reaction flask equipped with a distillation bridge and a stirrer 200 g of the aqueous solution of the 2'-FL raw material was heated by means of a water bath to 55° C. (bath temperature). At a pressure of 30 mbar 31.65 g of water were distilled off resulting in a syrup containing 62.4% by weight of 2'-FL. The weight ratio of product (2'-FL) to water in the obtained syrup was 2.3:1. The resulting viscous solution was expanded to ambient pressure and allowed to cool to 45° C. (bath temperature) and seeded with 0.05 g of crystalline 2'-FL obtained from example 1 (Form A). The mixture was stirred at 45° C. (bath temperature) and ambient pressure for further 4 h and then cooled to 10°. A sample was taken which showed that form A of 2'-FL had been formed. Then 136.2 ml of acetic acid was added within 30 min while keeping the temperature at 10° C., such that the volume ratio of acetic acid and water was 3:1 v/v. The obtained suspension was stirred for 0.5 h at 10° C. at ambient pressure. The thus obtained suspension filtered through a suction filter and the filter cake was washed 3 times with each 10 ml of acetic acid/water (80/20 w/w) and thereafter dried at 40° C. and 0.8 mbar for 12 h. Thereby, 53.6 g (yield 49.1%) of crystalline material having the following composition was obtained:
Composition (HPLC): 0.5% DiFL and 96.2% 2'-FL (no detectable amounts of lactose and fucosyllactulose). The obtained crystalline material contained 3.9% by weight of water as determined by Karl-Fischer titration.
In the obtained crystalline material 2'-FL was present essentially as form A, as determined by PXRD.

Example 3

In a reaction flask equipped with a distillation bridge and a stirrer 200 g of the aqueous solution of the 2'-FL raw material was heated by means of a water bath to 65° C. (internal temperature; 80° C. bath temperature). At a pressure of 250 mbar 38 g of water were distilled off resulting in a syrup containing 64.8% by weight of 2'-FL. The weight ratio of product (2'-FL) to water in the obtained syrup was 2.5:1. The resulting syrup was expanded to ambient pressure and allowed to cool to 50° C. (bath temperature). The suspension was stirred at 50° C. at ambient pressure (bath temperature) for further 3 h and then cooled to 20° C. and stirred for further 1 h at 20° C. Then 117 ml of acetic acid was added within 30 min while keeping the temperature at 20° C., such that the volume ratio of acetic acid and water was 3:1 v/v. The obtained suspension was stirred for 0.5 h at 10° C. The thus obtained suspension filtered through a suction filter and the filter cake was washed 3 times with each 15 ml of acetic acid/water (80/20 w/w) and thereafter dried at 40° C. and 0.8 mbar for 12 h. Thereby, 80.3 g (yield 75.6%) of crystalline material having the following composition was obtained:
Composition (HPLC): 0.2% lactose, 0.3% fucosyllactulose and 98.8% 2'-FL (no detectable amounts of DiFL). The obtained crystalline material contained 0.015% by weight of water as determined by Karl-Fischer titration.

In the obtained crystalline material 2'-FL was present essentially as form II, as determined by PXRD As variations to example 3 above the following are possible:
a. Instead of increasing the concentration of 2'-FL in the syrup above 60% by weight as detailed in example 3, it is also possible to use less concentrated syrups of 2'-FL with concentrations of only up to 50% by weight of 2'-FL. The results of the experiment performed starting from those less concentrated solutions is basically the same as in example 3.
b. As a further possibility, the amount of acetic acid as used in example 3 can be increased in its amounts up to 3-fold, still leading to the basically same results as in example 3.
c. As a further possibility, the solution could be seeded with any polymorphic form of 2'-FL and even with amorphous 2'-FL also yielding the basically same results.

"Basically the same results" means that the absolute amounts of the purity of 2'-FL and the contents of the by-products vary to a very small extent, i.e. about less than 5% deviation from the experimental results of example 3.

In example 4 an aqueous solution of a 2'-FL raw material was used, which was obtained by fermentation and subsequent downstream processing including passing the fermentation broth through a bed of an ion exchange resin and concentration of the thus treated broth to a solids content of 61.5% by weight was used. The aqueous solution contained 49.4% by weight of 2'-FL and 12.1% by weight of mono- and oligosaccharides including 0.8% of lactose, 0.4% of fucosyllactulose and 2.5% of DiFL.

Example 4

In a reaction flask equipped with a distillation bridge and a stirrer 200 g of the aqueous solution of the 2'-FL raw material was heated by means of a water bath to 45° C. (bath temperature). At a pressure of 20-50 mbar about 30 g of water were distilled off resulting in a syrup containing about 58% by weight of 2'-FL. The weight ratio of product (2'-FL) to water in the obtained syrup was 2.1:1. The resulting viscous syrup was expanded to ambient pressure and seeded 45° C. (bath temperature) with 0.05 g of crystalline 2'-FL obtained from example 3 (Form II). The mixture was stirred at ambient pressure and 45 ° C. (bath temperature) for further 16 h. The thus obtained thick suspension was discharged from the reactor and filtered through a heated suction filter (40° C.) and the filter cake was dried at 40° C. and 10 mbar for 16 h under a flow of inert gas. Thereby, 78.1 g of crystalline material (yield 69.3%) having the following composition was obtained:

Composition (HPLC): 0.72% lactose, 0.57% fucosyllactulose, 2.61% DiFL and 87.64% 2'-FL. The obtained crystalline material contained 3.0% by weight of water as determined by Karl-Fischer titration.

In the obtained crystalline material 2'-FL was present essentially as form A, as determined by PXRD.

In the following examples 5 to 8 and comparative examples C1 and C2 an aqueous solution of a 2'-FL raw material was used, which was obtained by fermentation and subsequent downstream processing including decolorization, microfiltration, ultrafiltration, demineralization and reverse osmosis. The aqueous solution had a dry matter content of 25% by weight and contained 21.0% by weight of 2'-FL and 4% by weight of mono- and oligosaccharides including lactose and DiFL.

Example 5

In a rotary evaporator the aqueous solution of a 2'-FL raw material was evaporated at 60° C. under reduced pressure to a dry matter content of about 73% by weight and a concentration of 2'-FL of about 59% by weight. 1517 g of the thus obtained solution were filled into a baffled tank and stirred at 60° C. (internal temperature). Then, 12 g of amorphous 2'-FL were added to this solution and formation of solids was observed. The thus formed suspension was stirred for 20 h at 60° C. (internal temperature).Then, the thus formed suspension was cooled within 1.5 h to 25° C. with stirring. The thus obtained suspension was then filtered without washing. Thereby, 467 g of a wet crystalline material having the following composition was obtained:

Composition of the filter cake: 83% b.w. 2'-FL, 1.2% b.w. lactose, 0.9% b.w. fucosyllactulose, 2.1% b.w. DiFL and 9% b.w. water. In filter cake 2'-FL was present essentially as form II, as determined by PXRD. The calculated yield was 42% based on the fucosyllactose contained in the concentrated solution.

The filtrate had the following composition: 49% b.w. 2'-FL, 1.4% b.w. fucosyllactulose, 2% b.w. lactose, 3.7% b.w. DiFL and 36% b.w. water.

The filter cake resistance was $5 \times 10^{12}$ Pas/m$^2$.

The same variations a and c as mentioned in the context of example 3 are here applicable as well, leading to the basically same results as in example 5.

Example 6

In a rotary evaporator the aqueous solution of a 2'-FL raw material was evaporated at 40° C. under reduced pressure to a dry matter content of about 62% by weight and a concentration of 2'-FL of about 50% by weight. 1532 g of the thus obtained solution were filled into a baffled tank and stirred at 40° C. (internal temperature). Then, 5 g of crystalline 2'-FL (form II) were added to this solution and formation of solids was observed. The thus formed suspension was stirred for 19 h at 40° C. (internal temperature).Then, the thus formed suspension was evaporated at 40° C. under reduced pressure to a concentration of 2'-FL of 61% by weight and thereafter cooled within 1.0 h to 25° C. with stirring. The suspension was stirred for further 22 h at 25° C. The thus obtained suspension was then filtered without washing. Thereby, 772 g of wet crystalline material having the following composition was obtained:

Composition of the filter cake: 77% b.w. 2'-FL, 1.1% b.w. lactose, 0.8% b.w. fucosyllactulose, 1.9% b.w. DiFL and 15% b.w. water. The calculated yield was 77% based on the 2'-FL contained in the concentrated solution. In filter cake 2'-FL was present essentially as form B, as determined by PXRD.

The filtrate had the following composition: 36% b.w. 2'-FL, 2% b.w. fucosyllactulose, 3.1% b.w. lactose, 5% b.w. DiFL and 40% b.w. water.

The filter cake resistance was $4 \times 10^{11}$ Pas/m$^2$.

Example 7

In a rotary evaporator the aqueous solution of a 2'-FL raw material was evaporated at 40° C. under reduced pressure to a dry matter content of about 65% by weight and a concentration of 2'-FL of about 52% by weight. 1572 g of the thus obtained solution were filled into a baffled tank and stirred at 40° C. (internal temperature). Then, 26 g of crystalline 2'-FL (form A) were added to this solution and formation of solids was observed. The thus formed suspension was stirred for 1 h at 40° C. (internal temperature).Then, the thus formed suspension was evaporated at 40° C. under reduced pressure to a concentration of 2'-FL of 55% by weight followed by stirring for 12 h at 40° C. and subsequent cooling within 1.0 h to 25° C. with stirring. The suspension was stirred for further 7 h at 25° C. The thus obtained suspension was then filtered without washing. Thereby, a wet crystalline material was obtained, which contained 2'-FL as its form B, as determined by PXRD.

After drying the filter cake for 2 days at 60° C. and 100 mbar crystalline material having the following composition was obtained:

90% b.w. 2'-FL, 0.5% b.w. lactose, 0.3% b.w. fucosyllactulose, 1.1% b.w. DiFL and 5.9% b.w. water. The calculated yield was 41% based on the 2'-FL contained in the concentrated solution. In the dry crystalline material 2'-FL was present essentially as form A, as determined by PXRD.

The filtrate had the following composition: 45% b.w. 2'-FL, 1.3% b.w. fucosyllactulose, 1.9% b.w. lactose, 3.7% b.w. DiFL and 39% b.w. water.

The filter cake resistance was $5 \times 10^{11}$ Pas/m$^2$.

Example 8

The filtrates obtained in examples 5, 6 and 7 and water to a total of 1099 g were filled into a baffled tank and stirred at 40° C. The concentration of 2'-FL in this solution was 36% by weight. Stirring was continued while water was evaporated from the solution at 40° C. under reduced pressure until the concentration of 2'-FL was 43% by weight (dry matter content was 67% by weight). Then, 8 g of crystalline 2'-FL (form A) were added to this solution and formation of solids was observed. The thus formed suspension was stirred for 2 h at 40° C. (internal temperature).Then, the thus formed suspension was evaporated at 40° C. under reduced pressure to a concentration of 2'-FL of 47% by weight followed by stirring for 1 h at 40° C. and subsequent cooling within 1.0 h to 25° C. with stirring. The suspension was stirred for further 72 h at 25° C. The thus obtained suspension was then filtered without washing. Thereby, a wet crystalline material was obtained, which contained 2'-FL as its form B.

After drying the filter cake for 2 days at 60° C. and 100 mbar crystalline material having the following composition was obtained:

88% 2'-FL, 0.9% b.w. lactose, 0.5% b.w. fucosyllactulose and 1.7% b.w. DiFL. The calculated yield was 26% based on the 2'-FL contained in the concentrated solution. In the dry crystalline material 2'-FL was present essentially as form A, as determined by PXRD.

The filtrate had the following composition: 40% b.w. 2'-FL, 2.1% b.w. fucosyllactulose, 3.2% b.w. lactose, 5.7% b.w. DiFL and 35% b.w. water.

The filter cake resistance was $6 \times 10^{11}$ Pas/m$^2$.

Comparative Example C1

In a distillation apparatus the aqueous solution of a 2'-FL raw material was evaporated at 60° C. under reduced pressure to a concentration of 2'-FL of about 42% by weight. 1663 g of the thus obtained solution were filled into a baffled tank and evaporated at 60° C. under reduced pressure to a dry matter content of 85% by weight and concentration of 2'-FL of 69%. Then spontaneous crystallization occurred and the viscosity of the suspension was too high to drain it off the baffled tank. A PXRD of the suspension showed that the 2'-FL was present essentially as form II.

Comparative Example C2

In a distillation apparatus the aqueous solution of a 2'-FL raw material was evaporated at 50° C. under reduced pressure to a concentration of 2'-FL of about 50% by weight. 1607 g of the thus obtained solution were filled into a baffled tank and evaporated at 40° C. under reduced pressure to a dry matter content of 80% by weight and concentration of 2'-FL of 65%. Then spontaneous crystallization occurred and the viscosity of the suspension was too high to drain it off the baffled tank. A PXRD of the suspension showed that the 2'-FL was present essentially as form B.

In the following examples 9 to 10 an aqueous solution of a 2'-FL raw material was used, which was obtained by fermentation and subsequent downstream processing including decolorization, microfiltration, ultrafiltration, demineralization and reverse osmosis. The aqueous solution had a dry matter content of 29% by weight and contained 24.5% by weight of 2'-FL and 4% by weight of mono- and oligosaccharides including lactose and DiFL.

The aqueous solution of a 2'-FL raw material was concentrated in a rotary evaporator under reduced pressure to a concentration of 2'-FL of about 52.1% by weight. The solution is termed "pre-evaporated feed" and was used in the following examples 9 and 10.

Example 9

1612 g of pre-evaporated feed were filled into a baffled tank and stirred at 60° C. (internal temperature). Water was evaporated under reduced pressure with stirring at 60° C. to a concentration of 62% be weight of 2'-FL. Then, 12 g of crystalline 2'-FL (form II), suspended in a small volume of the pre-evaporated feed, were added to this solution and formation of solids was observed. The thus formed suspension was stirred for 19 h at 60° C. (internal temperature) with stirring at 450 rpm. Then, the thus formed suspension was filtered without washing by using a heated pressure nutsche (60° C., pressure difference 0.5 bar, 230 s). Thereby, a wet crystalline material was obtained, which contained 2'-FL as its form II as evidenced by PXRD.

The filter cake was dried for 1 day at 60° C. and 100 mbar. The obtained crystalline material had the following composition: 94.6% b.w. 2'-FL, 0.8% b.w. lactose, 2.1% b.w. DiFL. The calculated yield was 45% based on the 2'-FL contained in the concentrated solution.

The same variations a and c as mentioned in example 3 are here applicable as well, leading to the basically same results as in example 9.

Example 10

1628 g of pre-evaporated feed were filled into a baffled tank and stirred at 40° C. (internal temperature). Water was evaporated under reduced pressure with stirring at 40° C. to a concentration of 63% be weight of 2'-FL. Then, 13 g of crystalline 2'-FL (form A), suspended in a small volume of the pre-evaporated feed, were added to this solution and formation of solids was observed. The thus formed suspension was stirred for 21 h at 40° C. (internal temperature) with stirring at 450 rpm. Then, the thus formed suspension was filtered without washing by using a heated pressure nutsche (40° C., pressure difference 0.5 bar, 403 s). Thereby, a wet crystalline material was obtained, which contained 2'-FL as its form B as evidenced by PXRD.

The filter cake was dried for 1 day at 60° C. and 100 mbar. The obtained crystalline material had the following composition: 88% b.w. 2'-FL, 1.4% b.w. lactose, 4.3% b.w. DiFL. The calculated yield was 80% based on the 2'-FL contained in the concentrated solution. PXRD of the dried crystalline material showed that 2'-FL was essentially present as form A, as determined by PXRD.

Example 11

An aqueous solution of a 2'-FL raw material was used, which was obtained by fermentation and subsequent downstream processing including passing the fermentation broth through a bed of an ion exchange resin and concentration of the thus treated broth to a 2'-FL content of 50.4% by weight. The aqueous solution additionally contained 0.9% by weight of lactose, 2.9 by weight of DiFL and 1.6% by weight of fucosyllactulose.

In a reaction flask equipped with a distillation bridge and a stirrer 150 g of the aqueous solution of the 2'-FL raw material was heated by means of a water bath to 50° C. (bath temperature). At a pressure of 30-100 mbar water was distilled off resulting in a syrup containing 65% by weight of 2'-FL. The vessel was expanded to ambient pressure and the resulting viscous solution was allowed to cool to 45° C. (bath temperature) and seeded with 0.15 g of crystalline 2'-FL obtained from a previous run. The mixture was stirred at 45° C. (bath temperature) for further 4 h, allowed to cool to RT and stirred for further 30 h at RT. To the thus obtained thick suspension 84 g of glacial acetic acid were added and the mixture was stirred for further 3 h to complete crystallization. The suspension was filtered through a suction filter and the filter cake was washed 3 times with glacial acetic acid and thereafter dried at 40° C. and 1.0 mbar for 12 h. Thereby, 61 g of crystalline material having the following composition was obtained:

Composition (HPLC): 92.9% 2'-FL, 0.1% lactose, 0.1% fucosyllactulose, 0.4% DiFL and 0.6% acetic acid. The obtained crystalline material contained 3.6% by weight of water as determined by Karl-Fischer titration.

In the obtained crystalline material 2'-FL was present essentially as form A, as determined by PXRD.

We claim:

1. Method for selectively obtaining crystalline form A or form B of 2'-fucosyllactose from a 2'-fucosyllactose raw material, which contains 2'-FL as a main constituent and at least 0.5% by weight, based on the total amount of mono- and oligosaccharides in the raw material, of one or more mono-or oligosaccharides different from 2'-fucosyllactose, where the method comprises
    a) providing a solution of the 2'-fucosyllactose raw material in water, which does not contain more than 10% by weight of organic solvents, based on the total amount of water;
    b) effecting the crystallization of 2'-fucosyllactose at a temperature in the range from 0 to 52° C. by inducing conditions of a controlled supersaturation in the solution, where form A or form B of 2'-fucosyllactose is obtained and a water miscible organic solvent is added to the suspension when the crystallization is almost complete; and
    c) separating crystalline form A or form B of 2'-fucosyllactose from the mother liquor;
    and where during controlled supersaturation in step b) not more than 10% by weight of organic solvents are present, based on the total amount of water present during step b).

2. The method of claim 1, where the conditions of a controlled supersaturation are induced in a manner such that the ratio c:c* of the concentration c of dissolved 2'-fucosyllactose to the equilibrium solubility c* of 2'-fucosyllactose under the conditions of controlled supersaturation is from more than 1:1 to 1.5:1, thereby effecting the crystallization of 2'-fucosyllactose.

3. The method of claim 1, where the controlled supersaturation is induced by removing water and/or by cooling.

4. The method of claim 1, where the crystallization is effected in the presence of solid 2'-fucosyllactose and is carried out as an evaporation crystallization.

5. The method of claim 1, where the concentration of dissolved 2'-fucosyllactose under the conditions of controlled supersaturation is in the range from 400 to 750 g/L.

6. The method of claim 1, where the 2'-fucosyllactose raw material contains at least one oligosaccharide selected from lactose, difucosyllactose, lactulose and fucosylated lactulose.

7. The method of claim 1, where the solution of 2'-fucosyllactose provided in step a) does not contain more than 5000 ppm of solid insoluble material, based on the total weight of the solution.

8. The method of claim 1, where the aqueous solution of 2'-fucosyllactose provided in step a) is obtained by a fermentation process.

9. The method of claim 1, where the aqueous solution of 2'-fucosyllactose provided in step a) is fed to a continuously operated crystallization apparatus, which contains an aqueous suspension of 2'-fucosyllactose crystals.

10. The method of claim 9, where step b) comprises
    b1) continuously feeding the aqueous solution of 2'-fucosyllactose to a crystallization apparatus containing an aqueous suspension of 2'-fucosyllactose;
    b2) continuously removing water from the aqueous suspension of 2'-fucosyllactose contained in the crystallization apparatus to maintain conditions of controlled supersaturation;
    b3) continuously removing the aqueous suspension of 2'-fucosyllactose from the crystallization apparatus.

11. The method of claim 9, where a portion of the aqueous suspension of 2'-fucosyllactose removed in step b3) is mixed with the aqueous solution of 2'-fucosyllactose of step b1) and the mixture is fed back it into the crystallization apparatus.

12. The method of claim 1, where the solution of the 2'-fucosyllactose raw material is subjected to a crystallization in batch- or fed-batch operated crystallization apparatus.

13. The method of claim 1, where the crystallization is carried out at a temperature in the range from 20 to 52° C. in the presence of solid 2'-fucosyllactose and where the crystallization is effected from an aqueous supersaturated solution under the conditions of controlled supersaturation, where the aqueous supersaturated solution has a concentration of dissolved 2'-fucosyllactose in the range from 410 to 630 g/L.

14. The method of claim 1, where at least a portion of the mother liquor obtained in step c) is subjected to a crystallization of 2'-fucosyllactose by inducing conditions of a controlled supersaturation in the mother liquor.

15. The method of claim 14, where at least a portion of the mother liquor is mixed with the solution of the 2'-fucosyllactose raw material prior to carrying out step b).

16. The method of claim 1, which comprises a first crystallization step and a second crystallization step,
- where the aqueous solution of the 2'-fucosyllactose raw material provided in step a) is subjected to a crystallization of the second crystallization step,
- where in the second crystallization step the crystallization of 2'-fucosyllactose is effected by inducing conditions of a controlled supersaturation in the solution according to step b), where the aqueous suspension of the crystalline 2'-fucosyllactose obtained in the second crystallization step is subjected to a solid-liquid separation to obtain a crystalline 2'-fucosyllactose and a mother liquor,
- where the mother liquor obtained in the solid-liquid separation is introduced into the first crystallization step.

17. The method of claim 16, where the crystalline 2'-fucosyllactose obtained in the first crystallization step is dissolved in the aqueous solution of the 2'-fucosyllactose raw material prior to carrying out the second crystallization step.

* * * * *

UNITED STATES PATENT AND TRADEMARK OFFICE
CERTIFICATE OF CORRECTION

Page 1 of 1

PATENT NO. : 11,685,759 B2
APPLICATION NO. : 17/286474
DATED : June 27, 2023
INVENTOR(S) : Michael Puhl et al.

It is certified that error appears in the above-identified patent and that said Letters Patent is hereby corrected as shown below:

On the Title Page

Item (30) Foreign Application Priority Data should read:
Oct. 18, 2018 (EP)...............18201228
Nov. 15, 2018 (EP)...............18206491
Aug. 23, 2019 (EP)...............19193228

Signed and Sealed this
Twenty-second Day of July, 2025

Coke Morgan Stewart
*Acting Director of the United States Patent and Trademark Office*